(12) United States Patent
Senoh et al.

(10) Patent No.: US 10,906,869 B2
(45) Date of Patent: Feb. 2, 2021

(54) ORGANIC SULFUR MATERIAL AND METHOD FOR PRODUCING SAME

(71) Applicant: National Institute of Advanced Industrial Science and Technology, Tokyo (JP)

(72) Inventors: Hiroshi Senoh, Osaka (JP); Toshikatsu Kojima, Osaka (JP); Nobuhiko Takeichi, Osaka (JP); Hisanori Ando, Osaka (JP)

(73) Assignee: National Institute of Advanced Industrial Science and Technology, Tokyo (JP)

( * ) Notice: Subject to any disclaimer, the term of this patent is extended or adjusted under 35 U.S.C. 154(b) by 63 days.

(21) Appl. No.: 15/563,323

(22) PCT Filed: Mar. 31, 2016

(86) PCT No.: PCT/JP2016/060615
§ 371 (c)(1),
(2) Date: Sep. 29, 2017

(87) PCT Pub. No.: WO2016/159212
PCT Pub. Date: Oct. 6, 2016

(65) Prior Publication Data
US 2018/0065927 A1 Mar. 8, 2018

(30) Foreign Application Priority Data
Mar. 31, 2015 (JP) .................................. 2015-073622

(51) Int. Cl.
*H01M 10/052* (2010.01)
*H01M 10/054* (2010.01)
(Continued)

(52) U.S. Cl.
CPC ............ *C07C 381/00* (2013.01); *C01B 32/70* (2017.08); *C01B 32/75* (2017.08); *C08L 71/02* (2013.01);
(Continued)

(58) Field of Classification Search
CPC ............... H01M 10/0525; H01M 4/60; H01M 10/0562; H01M 4/38; H01M 4/5815;
(Continued)

(56) References Cited

U.S. PATENT DOCUMENTS

2011/0200875 A1\* 8/2011 Miyuki ............... H01M 4/1399
429/213
2014/0134485 A1 5/2014 Miyuki et al.
2016/0293955 A1 10/2016 Hochi et al.

FOREIGN PATENT DOCUMENTS

EP 3279140 A1 2/2018
JP 2003/123758 A 4/2003
(Continued)

OTHER PUBLICATIONS

Zhu, Pengyu. "Structure and Performance Relationship in High Performance Lithium Ion Battery Cathodes." (2013). (Year: 2013).\*
(Continued)

*Primary Examiner* — Milton I Cano
*Assistant Examiner* — Philip A. Stuckey
(74) *Attorney, Agent, or Firm* — Cesari & McKenna, LLP

(57) ABSTRACT

An organic sulfur material comprising carbon, hydrogen, oxygen, and sulfur as constituent elements, and having peaks in the vicinity of 482 cm−1, 846 cm−1, 1066 cm−1, 1279 cm−1, and 1442 cm−1 in a Raman spectrum detected by Raman spectroscopy, the peak in the vicinity of 1442 cm−1 being most intense, has a high capacity and high heat resistance, although a liquid organic starting material is used.

13 Claims, 24 Drawing Sheets

(51) Int. Cl.

| | |
|---|---|
| *C07C 381/00* | (2006.01) |
| *H01M 4/62* | (2006.01) |
| *H01M 4/38* | (2006.01) |
| *C01B 32/75* | (2017.01) |
| *H01M 4/58* | (2010.01) |
| *H01M 4/60* | (2006.01) |
| *H01M 10/0562* | (2010.01) |
| *C01B 32/70* | (2017.01) |
| *C08L 71/02* | (2006.01) |
| *G01N 21/65* | (2006.01) |
| *H01M 10/0525* | (2010.01) |

(52) U.S. Cl.
CPC .............. *G01N 21/65* (2013.01); *H01M 4/38* (2013.01); *H01M 4/5815* (2013.01); *H01M 4/60* (2013.01); *H01M 4/625* (2013.01); *H01M 10/052* (2013.01); *H01M 10/054* (2013.01); *H01M 10/0525* (2013.01); *H01M 10/0562* (2013.01); *Y02E 60/10* (2013.01); *Y02P 70/50* (2015.11); *Y02T 10/70* (2013.01)

(58) Field of Classification Search
CPC .. H01M 4/625; H01M 10/054; H01M 10/052; C07C 381/00; C08L 71/02; G01N 21/65; C01B 32/70; C01B 32/75; Y02P 70/54; Y02P 70/50; Y02T 10/7011; Y02T 10/70; Y02E 60/10
See application file for complete search history.

(56) References Cited

FOREIGN PATENT DOCUMENTS

| | | | |
|---|---|---|---|
| JP | 2003123758 A | * | 4/2003 |
| JP | 2011/028948 A | | 2/2011 |
| JP | 2012/028117 A | | 2/2012 |
| JP | 5142162 B | | 11/2012 |
| JP | 5164286 B | | 12/2012 |
| JP | 2014/096326 A | | 5/2014 |
| JP | 2015/005421 A | | 1/2015 |
| WO | WO-2010/044437 A1 | | 4/2010 |
| WO | WO-2012/132173 A1 | | 10/2012 |
| WO | WO-2013/001693 A1 | | 1/2013 |
| WO | WO-2015/050086 A1 | | 4/2015 |

OTHER PUBLICATIONS

Search Report issued to European counterpart application No. 16 773 092.8 by the EPO dated Sep. 19, 2018.
Ji et al "A Highly Ordered Nanostructured Carbon-Sulphur Cathode for Lithium-Sulphur Batteries" Nature Materials vol. 8, pp. 500-506, 2009.
Miyuki et al "Section 2.2: Sulfur-Based Cathode" The Latest Technological Trend of Rare Metal-Free Secondary Batteries, Sakai, pp. 81-101, 2013.
Trevey et al "Electrochemical Investigation of All-Solid-State Lithium Batteries with a High Capacity Sulfur-Based Electrode" Journal of the Electrochemical Society vol. 159, pp. A1019-A1022, 2012.
Larkin "Infrared and Raman Spectroscopy: Principles and Spectral Interpretation" Elsevier, 2011.

* cited by examiner

ORGANIC SULFUR MATERIAL AND METHOD FOR PRODUCING SAME

CROSS REFERENCE TO RELATED APPLICATIONS

This application is the National Stage of International Application No. PCT/JP2016/060615, filed on Mar. 31, 2016, which claims the benefit of Japanese Application No. 2015-073622, filed on Mar. 31, 2015. The contents of both applications are hereby incorporated by reference in their entirety.

TECHNICAL FIELD

The present invention relates to an organic sulfur material and a method for producing the organic sulfur material.

BACKGROUND ART

Recent years have seen technical advances in portable electronic devices, hybrid vehicles, etc., and there has been a growing demand for batteries (in particular, secondary batteries, such as lithium-ion secondary batteries) with a higher capacity for use in those devices and vehicles. However, the development of high-capacity cathodes for lithium-ion secondary batteries currently lags behind that of high-capacity anodes. Even actively researched and developed high-capacity Li (Ni, Mn, Co) $O_2$-based materials only have a capacity of about 250 to 300 mAh/g.

Sulfur, which has a theoretical capacity of as high as about 1672 mAh/g and has abundant resources, and which is inexpensive, is one of the promising candidates for high-capacity electrode materials. However, the use of elemental sulfur in battery systems using an organic electrolyte (e.g., lithium-ion secondary batteries) causes the problem of capacity reduction because lithium polysulfide formed during the charge and discharge process dissolves into the electrolyte solution and precipitates on the anode etc.

To solve this problem, a variety of attempts have been made by forming a composite of elemental sulfur with various organic materials, such as resins and pitch, and inhibiting dissolution and diffusion of lithium polysulfide into the electrolyte solution (e.g., Patent Literature (PTL) 1, PTL 2, and PTL 3, Non-Patent Literature (NPL) 1, NPL 2, and NPL 3). These sulfur-carbon composites have been reported as exhibiting a relatively high capacity and relatively excellent cycle characteristics. Until now, these sulfur-carbon composites have been produced by using, as a starting material of the carbon source, carbon materials, such as porous carbon; polyacrylonitrile (PAN); pitch; or other solid organic substances, and heating the starting material with elemental sulfur or with a sulfur-containing starting material. In particular, an organic sulfur material produced by using PAN as a starting material is referred to as a promising candidate as an electrode material that undergoes less cycle deterioration.

CITATION LIST

Patent Literature

PTL 1: JP5164286B
PTL 2: JP5142162B
PTL 3: WO 2010/044437

Non-Patent Literature

NPL 1: The Latest Technological Trend of Rare Metal-Free Secondary Batteries, supervised by Tetsuo Sakai, CMC Publishing Co., Ltd. (2013).
NPL 2: X. Ji et al., Nat. Mater., 8, 500 (2009).
NPL 3: J. E. Trevey et al., J. Electrochem. Soc., 159, A1019 (2012).

SUMMARY OF INVENTION

Technical Problem

Although the sulfur-carbon composites obtained by using resin, pitch, etc., as described above have excellent capacity and cycle characteristics, thermogravimetry and differential thermal analysis (TG-DTA) shows a weight loss from a temperature at around 250° C., indicating insufficient heat resistance. Moreover, PAN, which is usually used as a starting material, costs about 30000 yen per 100 g (about 270 dollars) and is a very expensive material.

Further, in terms of material synthesis, substances diffuse slowly in a reaction that uses a solid material, compared to reactions that use liquid materials or gaseous materials, and the reaction is thus likely to proceed more slowly than in reactions that use liquid materials or gaseous materials. To allow the reaction to efficiently proceed, it is preferable to liquefy or vaporize the solid material, or to use a liquid or gaseous material. Liquefaction or vaporization of a solid material requires a considerably high temperature, which is disadvantageous from the viewpoint of the manufacturing costs and the processes. Thus, performing a reaction using a liquid or gaseous material is a realistic approach; however, the use of an organic starting material in a liquid or gaseous form to produce an organic sulfur material in this manner has not even been considered.

The present invention has been made in view of the current status of the related art described above. The main object is to provide an organic sulfur material with a high capacity and high heat resistance by using an organic starting material in a liquid form.

Solution to Problem

The present inventors conducted extensive research to achieve the object and found that subjecting a solution containing polyethylene glycol or a derivative thereof and a sulfur-containing starting material to heat treatment in an inert atmosphere allows a high-temperature polyethylene glycol or a derivative thereof (liquid) to be brought into contact with the sulfur-containing starting material to thus allow a reaction to proceed, so that the liquid organic substance undergoes carbonization and efficiently incorporates sulfur, thus yielding an organic sulfur material having a high capacity and high heat resistance. Polyethylene glycol is very inexpensive, costing 3000 to 30000 yen per kilogram (about 27 to 270 dollars), which is less than one-tenth the cost of PAN. The thus obtained organic sulfur material has a Raman spectrum with characteristic peaks. The present invention has been accomplished through further research based on the above findings. Specifically, the present invention encompasses the following.

Item 1. An organic sulfur material comprising carbon, hydrogen, oxygen, and sulfur as constituent elements, and having peaks in the vicinity of 482 $cm^{-1}$, 846 $cm^{-1}$, 1066 $cm^{-1}$, 1279 $cm^{-1}$, and 1442 $cm^{-1}$ in a Raman spectrum detected by Raman spectroscopy, the peak in the vicinity of 1442 cm$^{-1}$ being most intense.

Item 2. The organic sulfur material according to Item 1, wherein the Raman scattering peak intensity in the vicinity of 482 cm$^{-1}$, the Raman scattering peak intensity in the vicinity of 846 cm$^{-1}$, the Raman scattering peak intensity in the vicinity of 1066 cm$^{-1}$, and the Raman scattering peak intensity in the vicinity of 1279 cm$^{-1}$ are all 0.4 times, or less, the Raman scattering peak intensity in the vicinity of 1442 cm$^{-1}$.

Item 3. The organic sulfur material according to Item 1 or 2, further having peaks of Raman scattering intensity in the vicinity of 770 cm$^{-1}$ and/or 1924 cm$^{-1}$ in the Raman spectrum detected by Raman spectroscopy.

Item 4. The organic sulfur material according to any one of Items 1 to 3, having peaks in the vicinity of 2469.2 eV, 2472.0 eV, and 2473.2 eV in an X-ray absorption fine structure spectrum, the peak intensity in the vicinity of 2472.0 eV and the peak intensity in the vicinity of 2473.2 eV being both 2 times, or more, the peak intensity in the vicinity of 2469.2 eV.

Item 5. The organic sulfur material according to any one of Items 1 to 4, wherein the carbon content is 20 to 50 wt %, the hydrogen content is 0.01 to 5 wt %, the oxygen content is 0.1 to 30 wt %, and the sulfur content is 45 to 75 wt %.

Item 6. A method for producing an organic sulfur material comprising carbon, hydrogen, oxygen, and sulfur as constituent elements, and having peaks in the vicinity of 482 cm$^{-1}$, 846 cm$^{-1}$, 1066 cm$^{-1}$, 1279 cm$^{-1}$, and 1442 cm$^{-1}$ in a Raman spectrum detected by Raman spectroscopy, the peak in the vicinity of 1442 cm$^{-1}$ being most intense, the method comprising the step of subjecting a solution containing a sulfur-containing starting material and polyethylene glycol or a derivative thereof to heat treatment in an inert atmosphere.

Item 7. The production method according to Item 6, wherein the heat treatment step comprises refluxing at 250° C. or higher the solution containing a sulfur-containing starting material and polyethylene glycol or a derivative thereof.

Item 8. The production method according to Item 6 or 7, wherein the method comprises the step of performing heating at 200 to 450° C. under an inert gas stream after the heat treatment step.

Item 9. An electrode active material for a battery, the material comprising the organic sulfur material of any one of Items 1 to 5 or the organic sulfur material obtained by the production method of any one of Items 6 to 8.

Item 10. The electrode active material for a battery according to Item 9, which is an electrode active material for a lithium-ion secondary battery or a sodium-ion secondary battery.

Item 11. A battery comprising, as a constituent element, the electrode active material for a battery of Item 9 or 10.

Item 12. The battery according to Item 11, which is a lithium-ion secondary battery or a sodium-ion secondary battery.

Item 13. An all-solid-state lithium-ion secondary battery or an all-solid-state sodium-ion secondary battery, comprising as constituent elements, the electrode active material for a battery of Item 9 or 10, and a lithium-ion conductive solid electrolyte or a sodium-ion conductive solid electrolyte.

Item 14. The all-solid-state lithium-ion secondary battery or the all-solid-state sodium-ion secondary battery according to Item 13, wherein the lithium-ion conductive solid electrolyte or the sodium-ion conductive solid electrolyte contains an inorganic compound containing sulfur as a constituent element.

Advantageous Effects of Invention

In the organic sulfur material of the present invention, sulfur is trapped within pores of carbon obtained by heating (in particular, calcining) an organic substance and is thus unlikely to vaporize even at a temperature as high as 400° C., which can inhibit dissolution and diffusion of sulfur released as lithium polysulfide into the electrolyte solution at the time of lithium insertion and extraction during charge and discharge. For this reason, the organic sulfur material of the present invention exhibits excellent charge-discharge characteristics (in particular, high capacity), as well as excellent heat resistance. Moreover, the organic sulfur material of the present invention may also possibly exhibit excellent cycle characteristics.

Accordingly, the organic sulfur material of the present invention is useful as an electrode active material (in particular, as a cathode active material) for a battery, such as a lithium-ion secondary battery.

Further, the production method of the present invention is capable of producing an organic sulfur material that exhibits excellent performance described above by using a liquid organic starting material, which has never been reported before.

DESCRIPTION OF EMBODIMENTS

1. Organic Sulfur Material

Figure 1:
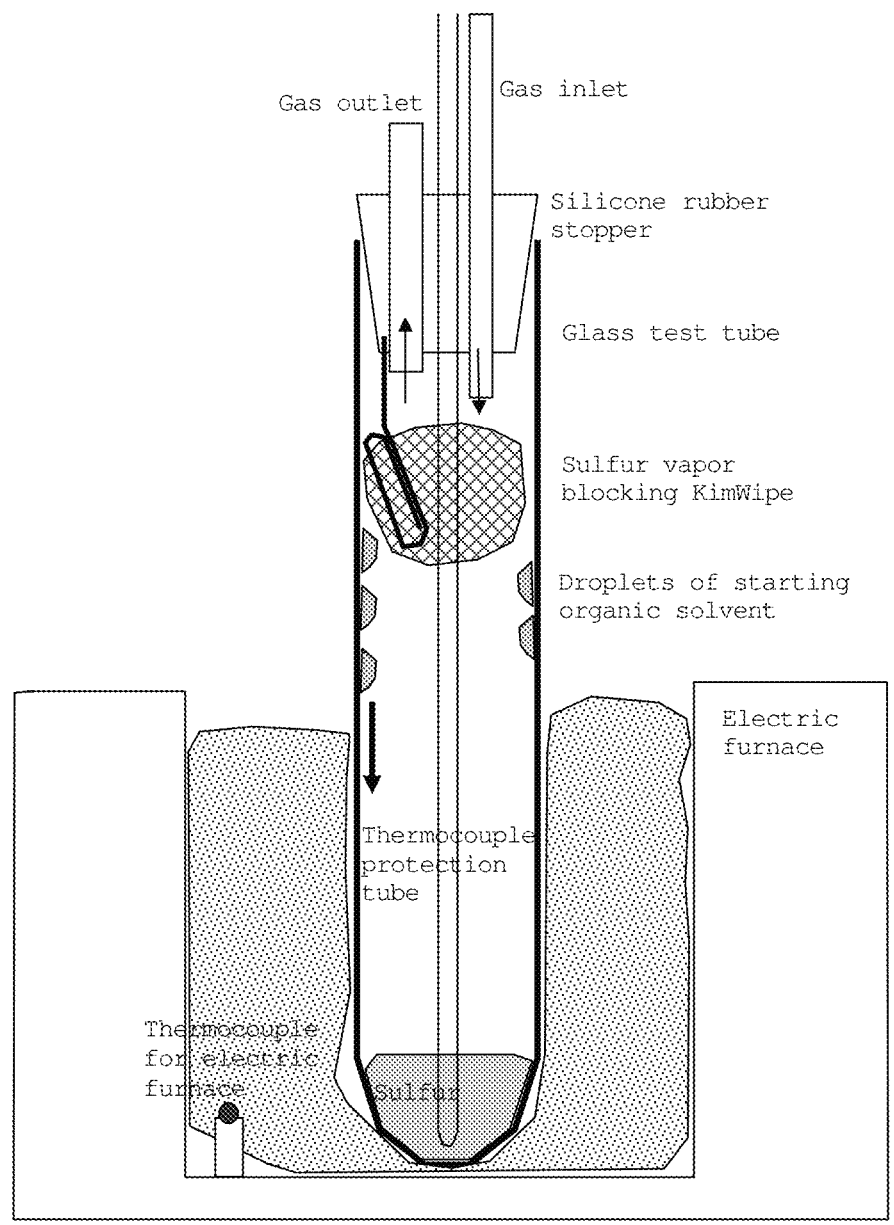
FIG. 1 is a cross-sectional schematic view showing one example of the device used in the production method of the present invention.

The organic sulfur material of the present invention has peaks in the vicinity of 482 $cm^{-1}$, 846 $cm^{-1}$, 1066 $cm^{-1}$, 1279 $cm^{-1}$, and 1442 $cm^{-1}$ in the Raman spectrum detected by Raman spectroscopy, and the peak in the vicinity of 1442 $cm^1$ is the most intense peak.

In the organic sulfur material of the present invention, sulfur is chemically fixed in the pore of carboneous material originating from a starting material. The carbide originating from a starting material is preferably amorphous. In the organic sulfur material of the present invention, sulfur is presumably confined within a carbide skeleton formed from carbon atoms originating from polyethylene glycol, making it possible to reduce unreacted sulfur (free sulfur) that is not incorporated into the organic sulfur material and thus inhibit dissolution and diffusion of sulfur released as lithium polysulfide into the electrolyte solution at the time of lithium insertion and extraction during charge and discharge. For this reason, the organic sulfur material of the present invention exhibits excellent charge-discharge characteristics (high capacity and excellent cycle characteristics), as well as excellent heat resistance.

The organic sulfur material of the present invention comprises carbon, hydrogen, oxygen, and sulfur as constituent elements.

The population by weight of each element in the organic sulfur material of the present invention is not particularly limited. The carbon is preferably present to such a degree that high conductivity can be maintained, and the carbon, hydrogen, oxygen, and sulfur are preferably present to such a degree that S—S bonds can be formed sufficiently to hinder free sulfur generation and that they can be maintained inside the structure. From this viewpoint, the carbon content in the organic sulfur material of the present invention is preferably 20 to 50 wt % (in particular 25 to 45 wt %), the hydrogen content is preferably 0.01 to 5 wt % (in particular 0.1 to 4 wt %), the oxygen content is preferably 0.1 to 30 wt % (in particular 1 to 25 wt %), and the sulfur content is preferably 45 to 75 wt % (in particular 50 to 70 wt %).

In addition to carbon, hydrogen, oxygen, and sulfur, the organic sulfur material of the present invention may contain a small amount of heteroatoms, such as nitrogen and phosphorus, to an extent that the effects of the present invention are not impaired. If the content is 10 wt % or less, in particular 5 wt % or less, these heteroatoms have a limited impact on the charge-discharge characteristics.

The organic sulfur material of the present invention has peaks in the vicinity of 482 $cm^{-1}$, 846 $cm^{-1}$, 1066 $cm^{-1}$, 1279 $cm^{-1}$, and 1442 $cm^{-1}$ in a Raman spectrum detected by Raman spectroscopy, and the peak in the vicinity of 1442 $cm^{-1}$ is the most intense peak. In the present invention, Raman spectra are obtained by Raman spectroscopy.

The organic sulfur material of the present invention has an S—S bond, and thus has a peak in the vicinity of 482 $cm^{-1}$, which represents the S—S bond stretching vibration. This peak position has a tolerance of ±50 $cm^{-1}$, in particular ±30 $cm^{-1}$. Specifically, the organic sulfur material of the present invention has a peak between 432 and 532 $cm^{-1}$, in particular between 452 and 512 $cm^{-1}$.

The organic sulfur material of the present invention has a peak in the vicinity of 846 $cm^{-1}$. This peak position has a tolerance of ±50 $cm^{-1}$, in particular ±30 $cm^{-1}$. Specifically the organic sulfur material of the present invention has a peak between 796 and 896 $cm^{-1}$, in particular between 816 and 876 $cm^{-1}$.

The organic sulfur material of the present invention has a peak in the vicinity of 1066 $cm^{-1}$. This peak position has a tolerance of ±50 $cm^{-1}$, in particular ±30 $cm^{-1}$. Specifically, the organic sulfur material of the present invention has a peak between 1016 and 1116 $cm^1$, in particular between 1036 and 1096 $cm^{-1}$.

The organic sulfur material of the present invention has a peak in the vicinity of 1279 cm$^{-1}$. This peak position has a tolerance of ±50 cm$^{1}$, in particular ±30 cm$^{1}$. Specifically, the organic sulfur material of the present invention has a peak between 1229 and 1329 cm$^{-1}$, in particular between 1249 and 1309 cm$^{-1}$.

The organic sulfur material of the present invention has a peak in the vicinity of 1442 cm$^{-1}$. This peak position has a tolerance of ±50 cm$^{-1}$, in particular ±30 cm$^{-1}$. Specifically, the organic sulfur material of the present invention has a peak between 1392 and 1492 cm$^{-1}$, in particular between 1412 and 1472 cm$^{-1}$.

In the organic sulfur material of the present invention, the peak in the vicinity of 1442 cm$^{-1}$ is the most intense peak among these five different peaks. In this specification, "the most intense peak" refers to a peak with the highest peak intensity. In particular, the Raman scattering peak intensity in the vicinity of 482 cm$^{-1}$, the Raman scattering peak intensity in the vicinity of 846 cm$^{-1}$, the Raman scattering peak intensity in the vicinity of 1066 cm$^{-1}$, and the Raman scattering peak intensity in the vicinity of 1279 cm$^{-1}$ are preferably all 0.4 times, or less, and particularly preferably 0.35 times, or less, the Raman scattering peak intensity in the vicinity of 1442 cm$^{-1}$. If sulfur is treated with resin (e.g., PAN), pitch, or the like, as is conventionally done, two intense peaks would be likely to appear in the vicinity of 1331 cm$^{-1}$ and in the vicinity of 1548 cm$^{-1}$, and the most intense peak in the vicinity of 1442 cm$^{-1}$ would not appear.

The organic sulfur material of the present invention, which has the five different peaks in the Raman spectrum detected by Raman spectroscopy, preferably further has a peak or peaks of Raman scattering intensity in the vicinity of 770 cm$^{-1}$ and/or in the vicinity of 1924 cm$^{-1}$.

The peak position in the vicinity of 770 cm$^{-1}$ has a tolerance of ±50 cm$^{-1}$, in particular ±30 cm$^{-1}$. Specifically, the organic sulfur material of the present invention preferably has a peak between 720 and 820 cm$^{-1}$, in particular between 740 and 800 cm$^{-1}$.

The peak position in the vicinity of 1924 cm$^{-1}$ has a tolerance of ±50 cm$^{-1}$, in particular ±30 cm$^{-1}$. Specifically, the organic sulfur material of the present invention preferably has a peak between 1874 and 1974 cm$^{-1}$, in particular between 1894 and 1954 cm$^{-1}$.

The organic sulfur material of the present invention has peaks in the vicinity of 2469.2 eV, in the vicinity of 2472.0 eV, and in the vicinity of 2473.2 eV in an X-ray absorption fine structure (XAFS) spectrum, and the peak intensity in the vicinity of 2472.0 eV and the peak intensity in the vicinity of 2473.2 eV are both 2 times, or more, the peak intensity in the vicinity of 2469.2 eV.

The organic sulfur material of the present invention preferably has a peak in the vicinity of 2469.2 eV. This peak position has a tolerance of ±0.5 eV, in particular ±0.3 eV. Specifically, the organic sulfur material of the present invention preferably has a peak between 2468.7 and 2469.7 eV, in particular between 2468.9 and 2469.5 eV.

The organic sulfur material of the present invention preferably has a peak in the vicinity of 2472.0 eV. This peak position has a tolerance of ±0.5 eV, in particular ±0.3 eV. Specifically, the organic sulfur material of the present invention preferably has a peak between 2471.5 and 2472.5 eV, in particular between 2471.7 and 2472.3 eV.

The organic sulfur material of the present invention, which has an S—C bond and S—H bond, preferably has a peak in the vicinity of 2473.2 eV, which suggests transitions from the hybridized orbitals of S—C bond and S—H bond. This peak position has a tolerance of ±0.5 eV, in particular ±0.3 eV. Specifically, the organic sulfur material of the present invention preferably has a peak between 2472.7 and 2473.7 eV, in particular between 2472.9 and 2473.5 eV.

In the organic sulfur material of the present invention, the peak intensity in the vicinity of 2472.0 eV and the peak intensity in the vicinity of 2473.2 eV, from among the above three peaks, are both preferably 2 times, or more, and particularly 2.2 times, or more, the peak intensity in the vicinity of 2469.2 eV. The upper limit is not particularly limited. However, the peak intensity in the vicinity of 2472.0 eV and the peak intensity in the vicinity of 2473.2 eV are preferably both 5 times, or less, the peak intensity in the vicinity of 2469.2 eV. If sulfur is treated with resin (e.g., PAN), pitch, or the like, as is conventionally done, an intense peak would be likely to appear in the vicinity of 2471.7 eV, and no intense peak would appear in the vicinity of 2473.2 eV.

Although the organic sulfur material of the present invention satisfies the above requirements, other impurities may optionally be incorporated as long as the performance of the organic sulfur material is not impaired. Examples of the impurities include nitrogen and the like that can be incorporated into the starting materials or during the production. Additionally, a starting material residue (e.g., polyethylene glycol or a derivative thereof, and free sulfur), a reaction product that is not a target product of the present invention, and the like may also be incorporated as impurities. The amount of these impurities is not limited as long as the above performance of the organic sulfur material is not impaired, and is preferably 30 wt % or less, and more preferably 20 wt % or less, taking the total amount of the organic sulfur compound, which satisfies the above requirements, as 100 wt %.

2. Production Method of Organic Sulfur Material

Without limiting the present invention, the organic sulfur material of the present invention can be obtained by using a production method comprising the step of subjecting a solution containing a sulfur-containing starting material and polyethylene glycol or a derivative thereof to heat treatment (in particular, heat treatment by reduction) in an inert atmosphere. According to this method, it is possible to obtain an organic sulfur material in which the polyethylene glycol or a derivative thereof that has undergone carbonization and thus has conductivity is bonded to the sulfur-containing starting material, thereby suppressing generation of free sulfur. The following more specifically describes this method.

(2-1) Starting Material

In the present invention, a sulfur-containing starting material and polyethylene glycol or a derivative thereof are used as starting materials.

The sulfur-containing starting material is not particularly limited, and may contain, in addition to a sulfur element, elements that are to be released or volatilized during heat treatment (e.g., carbon, hydrogen, nitrogen, and oxygen). However, the sulfur-containing starting material preferably contains no metal element. Examples of the sulfur-containing starting material include sulfur (S) and the like. The sulfur-containing starting material may be used alone or in a combination of two or more.

The form of the sulfur-containing starting material is not particularly limited, and may be a solid or a liquid. As a solid, the sulfur-containing starting material is preferably a powder with an average particle size of about 0.1 to 100 µm. The average particle size of the starting material is determined as the value at which the cumulative frequency reaches 50% in particle size distribution measured by using a dry laser diffraction/scattering method. It is possible to use a starting material having a large particle size, and adjust the average particle size by pulverizing the material using a mortar or the like.

As polyethylene glycol or a derivative thereof, it is possible to use both polyethylene glycol and a derivative of polyethylene glycol. From the viewpoint of achieving higher capacity and higher heat resistance, the derivative of polyethylene glycol is preferably an alkyl ether of polyethylene glycol (in particular, a dimethyl ether of polyethylene glycol).

The average molecular weight of polyethylene glycol or a derivative thereof is preferably 90 to 20000, and more preferably 200 to 6000, considering that those with a lower molecular weight are more easily vaporized and released from the reaction system, and that its terminals are easily vaporized or removed.

Examples of the polyethylene glycol or a derivative thereof include polyethylene glycols having an average molecular weight of 200 to 20000; ethylene glycol; polyethylene glycol monoalkyl ethers (e.g., polyethylene glycol monomethyl ethers); glymes, such as monoglyme, diglyme, triglyme, tetraglyme, pentaglyme, octaglyme, and icosaglyme; polyethylene glycol-polypropylene glycol copolymers; higher molecular weight polyethylene oxides; and the like. These polyethylene glycols or a derivative thereof may be used alone or in a combination of two or more.

The mixing ratio of the sulfur-containing starting material to the polyethylene glycol or a derivative thereof is not particularly limited. Considering that the sulfur component turns into hydrogen sulfide ($H_2S$) and vaporizes during the reaction process, and considering that any residue of the sulfur-containing starting material can be removed in the heating step mentioned later, it is preferable that the sulfur-containing starting material be excessively contained, relative to the polyethylene glycol or a derivative thereof. The amount used of the polyethylene glycol or a derivative thereof is preferably adjusted in such a manner that the final product, i.e., an organic sulfur material, contains carbon (produced by carbonization of the polyethylene glycol or a derivative thereof), to an extent that sufficient conductivity is achieved. From this viewpoint, the amount used of the polyethylene glycol or a derivative thereof is preferably 10 to 100 parts by weight, more preferably 15 to 90 parts by weight, and still more preferably 20 to 50 parts by weight, per 100 parts by weight of the sulfur-containing starting material, although it depends on, for example, the carbon number of the polyethylene glycol or a derivative thereof, as well as the amount of sulfur contained in the sulfur-containing starting material. To use a large amount of the sulfur-containing starting material effectively, it is preferable to use a larger amount of the polyethylene glycol or a derivative thereof.

In the present invention, the sulfur-containing starting material and the starting material containing polyethylene glycol or a derivative thereof are preferably used in a liquid form. The polyethylene glycols, or a derivative thereof, that satisfy the above requirements are usually in a liquid form under the reflux conditions mentioned below; thus, when a sulfur-containing starting material and polyethylene glycol or a derivative thereof are mixed, a solution is obtained containing the sulfur-containing starting material and the polyethylene glycol or a derivative thereof. Even when polyethylene glycol or a derivative thereof is not a liquid at ordinary temperature, the polyethylene glycol or a derivative thereof may be used as a liquid at a reaction temperature of 250° C. or higher.

(2-2) Production Method of Organic Sulfur Material

In the production method of the present invention, the starting materials described above are used. Specifically, a solution containing a sulfur-containing starting material and polyethylene glycol or a derivative thereof is subjected to heat treatment (in particular, heat treatment by reduction) in an inert atmosphere. In the present invention, a solution containing a sulfur-containing starting material and polyethylene glycol or a derivative thereof is preferably refluxed at 250° C. or higher.

For example, as shown in FIG. 1, in the heat treatment performed by a reflux method, the starting material (a solution containing a sulfur-containing starting material and polyethylene glycol or a derivative thereof) is placed in a reactor (e.g., a test tube), and the upper part of the reactor is preferably cooled while the lower part of the reactor is heated in an electric furnace or the like. At this time, the reactor is preferably semi-sealed. If a longer test tube is used, a KimWipe is not required for locking sulfur vapor. In this process, the sulfur-containing starting material melts (or may stay as a solid) at the bottom of the reactor and reacts with the heated polyethylene glycol or a derivative thereof; and at the same time, the polyethylene glycol or a derivative thereof itself undergoes carbonization. The heated starting materials (the sulfur-containing starting material and polyethylene glycol or a derivative thereof) and a reaction intermediate partly vaporize once and return as reflux to the reaction system. As this process is repeated, the starting materials (the sulfur-containing starting material and polyethylene glycol or a derivative thereof) actively undergo a reaction, allowing the reaction to proceed efficiently. In this reaction process, carbonization of the polyethylene glycol or a derivative thereof presumably proceeds due to dehydration and/or dehydrogenation, and at the same time, sulfur is incorporated into the skeleton formed from carbon atoms originating from the polyethylene glycol or a derivative thereof. At this time, the yield is easily improved if the polyethylene glycol or a derivative thereof in a liquid form is added little by little to a reactor (e.g., a test tube) that contains the sulfur-containing starting material.

In this reflux method, the inert atmosphere is not particularly limited, and may be a nitrogen gas atmosphere, an argon gas atmosphere, or the like.

The reaction temperature and retention time in this reflux method are not particularly limited. Although it depends on the melting point, boiling point, etc., of the starting materials (a sulfur-containing starting material and polyethylene glycol or a derivative thereof), the reaction temperature is usually 250° C. or higher, preferably 300° C. or higher, more preferably 310 to 500° C., and still more preferably 330 to 450° C., and the retention time is usually 3 to 400 minutes, preferably 5 to 100 minutes, more preferably 10 to 60 minutes, and still more preferably 20 to 40 minutes. A reaction temperature within the above range allows each starting material to more sufficiently undergo a reaction to enable more sufficient carbonization of the polyethylene glycol or a derivative thereof and more sufficient incorporation of sulfur, which makes it possible to further reduce free sulfur and achieve higher capacity, and which, at the same time, makes it possible to further suppress volatilization of the polyethylene glycol or a derivative thereof with the sulfur-containing starting material and to more improve the yield of the reaction product. Further, a retention time within the above range allows each starting material to more sufficiently undergo a reaction to enable more sufficient carbonization of the polyethylene glycol or a derivative thereof and more sufficient incorporation of sulfur, which makes it possible to further reduce unreacted sulfur (free sulfur) and achieve higher capacity, and which, at the same time, makes it possible to further suppress volatilization of the polyethylene glycol or a derivative thereof with the sulfur-containing starting material and to more improve the yield of the reaction product. In the present invention, "retention time" refers to a time at the maximum temperature.

When the reflux reaction is performed in the above manner, it is possible to obtain the organic sulfur material of the present invention described later while reducing free sulfur remaining unreacted, although free sulfur may sometimes be contained. In this case, the free sulfur remaining unreacted is preferably vaporized and/or removed by heating the reaction product at 200 to 450° C. under an inert gas stream. In this manner, free sulfur is more reliably removed, enabling a further improvement of the conductivity and capacity. If free sulfur remains in the organic sulfur compound, the conductivity of the organic sulfur compound is reduced, and when charge and discharge are repeated in a battery system using an organic electrolyte solution, the sulfur is dissolved and diffused as lithium polysulfide in the electrolyte solution, causing a reduction in the capacity.

The inert gas used in this free sulfur removal process is not particularly limited, and nitrogen gas, argon gas, and the like may be used.

The flow rate of the inert gas at the time of performing this free sulfur removal process is not particularly limited, and is preferably 50 to 200 mL/min, and more preferably 100 to 150 mL/min, relative to 10 g of the crude product, from the viewpoint of removing the sulfur vapor generated upon heating, from the reaction product.

The reaction temperature and the retention time in the free sulfur removal process are not particularly limited. Although it also depends on the amount of the sulfur residue, the reaction temperature is usually a temperature at which sulfur vaporizes and/or sublimates, i.e., 200 to 450° C., preferably 250 to 350° C., and more preferably 270 to 330° C. The retention time is usually 0.5 to 5 hours, and preferably 1 to 3 hours.

3. Battery

The organic sulfur material of the present invention has excellent characteristics as described above. Taking advantage of the excellent characteristics, the organic sulfur material of the present invention is effectively used as ion conductors; electronic conductors; an electrode active material (in particular, a cathode active material) for lithium-ion batteries (in particular lithium-ion secondary batteries), such as lithium primary batteries, lithium-ion secondary batteries, and metal lithium secondary batteries; an electrode active material (in particular, a cathode active material) for sodium-ion secondary batteries; an electrode active material (in particular, a cathode active material) for magnesium-ion secondary batteries; an electrode active material (in particular, a cathode active material) for calcium-ion secondary batteries; an electrode active material (in particular, a cathode active material) for aluminum-ion secondary batteries; and the like. In particular, the organic sulfur material of the present invention is a high-capacity material having a high conductivity and excellent heat resistance, possibly achieves improved cycle characteristics, and is thus useful as an electrode active material for lithium-ion secondary batteries or sodium-ion secondary batteries (in particular, as a cathode active material for lithium-ion secondary batteries or an anode active material for sodium-ion secondary batteries).

A lithium-ion secondary battery or sodium-ion secondary battery comprising the organic sulfur material of the present invention as an electrode active material for a lithium-ion secondary battery or sodium-ion secondary battery (in particular, a cathode active material for a lithium-ion secondary battery or an anode active material for a sodium-ion secondary battery) may be used as a non-aqueous electrolyte lithium-ion secondary battery or non-aqueous electrolyte sodium-ion secondary battery containing, as an electrolyte, a non-aqueous solvent-based electrolyte solution, or may be used as an all-solid-state lithium-ion secondary battery containing, as an electrolyte, a lithium-ion conductive solid electrolyte or an all-solid-state sodium-ion secondary battery.

The non-aqueous electrolyte lithium-ion secondary battery, non-aqueous electrolyte sodium-ion secondary battery, all-solid-state lithium-ion secondary battery, and all-solid-state sodium-ion secondary battery may have the same structure as that of a known lithium-ion secondary battery or a known sodium-ion secondary battery, except for the use of the organic sulfur material of the present invention as an electrode active material.

For example, the non-aqueous electrolyte lithium-ion secondary battery and non-aqueous electrolyte sodium-ion secondary battery may have the same basic structure as that of a known non-aqueous electrolyte lithium-ion secondary battery and non-aqueous electrolyte sodium-ion secondary battery, except for the use of the organic sulfur material of the present invention described above as an electrode active material.

Regarding the cathode, the organic sulfur material of the present invention may be used as a cathode active material. For example, a positive electrode prepared by mixing the organic sulfur material of the present invention with a conductive material and a binder may be supported by a cathode collector, such as Al, Ni, stainless steel, or carbon cloth. Examples of usable conductive materials include carbon materials, such as graphite, cokes, carbon black, and acicular carbon. An anode may be an alkaline metal-containing material. For example, a metal lithium, a metal sodium, graphite into which lithium or sodium is doped, and the like may be used. These anode active materials may also optionally be supported by an anode collector, such as Al, Cu, Ni, stainless steel, or carbon, using the conductive materials described above, binders, etc.

When the organic sulfur material of the present invention is used as a cathode active material into which lithium or sodium has been doped beforehand, a material that does not contain lithium or sodium may be used as an anode. Examples include tin, silicon, alloys containing these metals, SiO, and the like, as well as graphite and sintering-resistant carbon. The organic sulfur material of the present invention may also be used as an anode active material.

When the organic sulfur material of the present invention is used as an anode active material, previously known materials may be used as a cathode, and existing materials such as lithium cobalt oxide ($LiCoO_2$), lithium nickel oxide ($LiNiO_2$), lithium manganese oxide ($LiMn_2O_4$), lithium iron phosphate ($LiFePO_4$), sodium ferrate ($LiFeO_2$), vanadium oxide-based materials, and sulfur-based materials may be used as a cathode active material.

Examples of separators for use include materials in the form of porous film, non-woven fabric, and woven fabric that are made of polyolefin resin, such as polyethylene and polypropylene, fluororesin, nylon, aromatic aramid, and inorganic glass.

Examples of electrolytes constituting a non-aqueous electrolyte solution include known electrolytes, such as lithium trifluoromethanesulfonyl amide (LiTFSA), lithium hexafluorophosphate ($LiPF_6$), and sodium hexafluorophosphate ($NaPF_6$).

Examples of solvents for non-aqueous electrolyte solutions include solvents known as a solvent for non-aqueous solvent-based secondary batteries, such as carbonates (e.g., ethylene carbonate, diethyl carbonate), ethers (e.g., tetraglyme), nitriles, and sulfur-containing compounds.

The all-solid-state lithium-ion secondary battery and all-solid-state sodium-ion secondary battery may also have the same structure as that of a known all-solid-state lithium-ion secondary battery and all-solid-state sodium-ion secondary battery, except for the use of the organic sulfur material of the present invention as an electrode active material (in particular, a cathode active material).

In this case, examples of usable lithium-ion conductive solid electrolytes and sodium-ion conductive solid electrolytes include polymer-based solid electrolytes such as polyethylene oxide-based polymers and polymers containing at least one of a polyorganosiloxane chain and a polyoxyalkylene chain; sulfide-based solid electrolytes; oxide-based solid electrolytes; and the like.

Regarding the cathode of all-solid-state lithium-ion secondary batteries and all-solid-state sodium-ion secondary batteries, the organic sulfur material of the present invention may be used as a cathode active material. For example, a positive electrode containing the organic sulfur material of the present invention, a conductive material, a binder, and a solid electrolyte may be supported by a cathode collector, such as Ti, Al, Ni, or stainless steel. Examples of usable conductive materials include carbon materials, such as graphite, cokes, carbon black, and acicular carbon, as with the non-aqueous electrolyte lithium-ion secondary batteries and non-aqueous electrolyte sodium-ion secondary batteries. When the organic sulfur material of the present invention is used as an anode active material, existing materials such as lithium cobalt oxide ($LiCoO_2$), lithium nickel oxide ($LiNiO_2$), lithium manganese oxide ($LiMn_2O_4$), lithium iron phosphate ($LiFePO_4$), vanadium oxide-based materials, and sulfur-based materials may be used as a cathode active material.

An anode for use may be a lithium- or sodium-containing material, or a lithium- or sodium-free material, as with the non-aqueous electrolyte lithium-ion secondary batteries or the non-aqueous electrolyte sodium-ion secondary batteries. Examples include tin, silicon, alloys containing these metals, SiO, and the like, as well as graphite and sintering-resistant carbon. These anode active materials may also optionally be supported by an anode collector, such as Al, Cu, Ni, stainless steel, or carbon, using the conductive materials described above, binders, etc. The organic sulfur material of the present invention may also be used as an anode active material.

There is also no particular limitation on the shape of non-aqueous electrolyte lithium-ion secondary batteries, non-aqueous electrolyte sodium-ion secondary batteries, all-solid-state lithium-ion secondary batteries, and all-solid-state sodium-ion secondary batteries. These batteries may have any shape, such as a cylindrical shape or prismatic shape.

EXAMPLES

The present invention is described below in more detail with reference to Examples. However, the present invention is, needless to say, not limited to these Examples.

Example 1

Polyethylene Glycol 200

Sulfur (Kishida Chemical Co., Ltd., 99%) (5.1051 g) and 1.0256 g of polyethylene glycol (Kishida Chemical Co., Ltd., average molecular weight: 190 to 210) were placed in a test tube (produced by Maruemu Corporation, A-30, 30 mm (diameter)×200 mm (length)), and a silicone rubber stopper provided with a nitrogen gas inlet, a gas outlet, and an alumina protective tube (SSA-S, inner diameter: 2 mm, outer diameter: 4 mm, length: 230 mm) for inserting a thermocouple was attached (FIG. 1). The lower part of the test tube, 100 mm from the bottom, was placed in the heating portion of an electric furnace, a heat insulation material was inserted into the furnace to secure the test tube, and the upper part of the test tube was left exposed to open air. A thermocouple (type K) was inserted into the alumina protective tube, and the temperature of the sample was measured. Nitrogen gas was introduced at a rate of 50 mL per minute, and the exhaust gas was led to an Erlenmeyer flask containing 100 mL of 10% sodium hydroxide to collect hydrogen sulfide from the generated gas. The electric furnace set temperature was gradually increased to 500° C. over a period of 20 minutes, and heating was performed for 1 hour until no liquid coagulation was observed inside the test tube, and until the sample temperature reached 443° C. After cooling, the reaction product was collected from the test tube and placed in a quartz boat, which was disposed inside a quartz tube (inner diameter: 30 mm, length: 900 mm) to allow sulfur to be vaporized and removed at 300° C. for 2 hours under nitrogen stream. In this manner, 0.1147 g of black solid powder was obtained.

According to elemental analysis of the obtained sample performed using a device that simultaneously quantifies carbon, hydrogen, and nitrogen, an O micro corder, and ion chromatography, the carbon content was 35.3 wt %, the hydrogen content was 0.4 wt %, the oxygen content was 2.9 wt %, the sulfur content was 61.4 wt %, and the nitrogen content was 0.0 wt % (not present).

Figure 2:
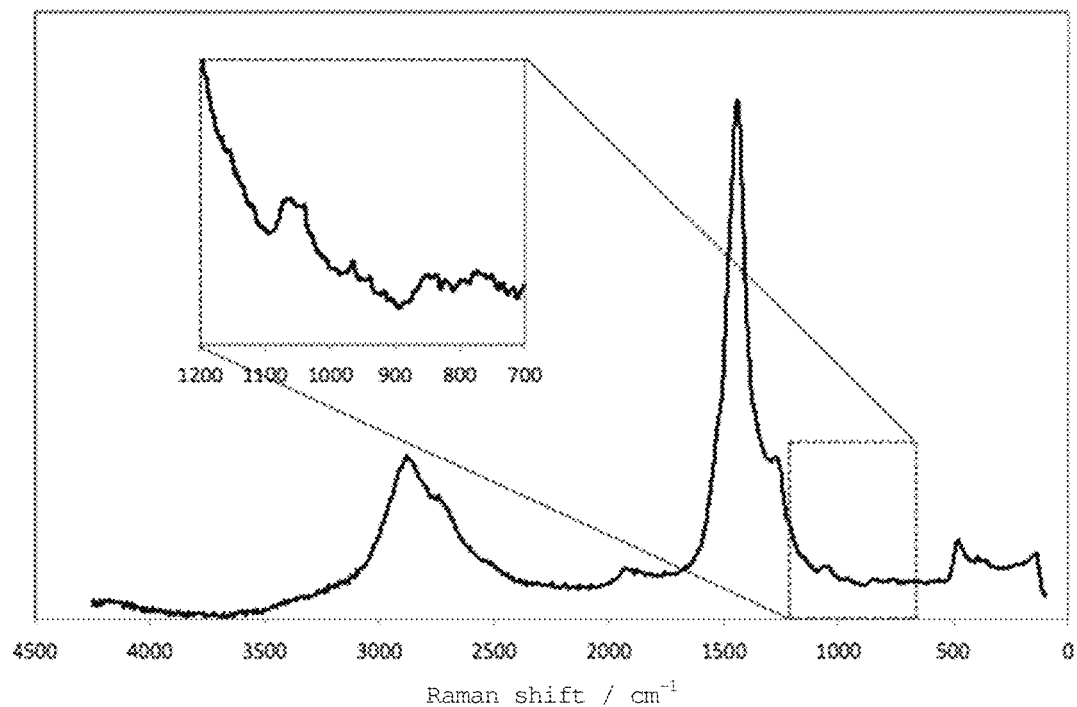
FIG. 2 is a graph showing a Raman spectrum (100-4250 cm$^{-1}$) of the organic sulfur material obtained in Example 1.

As shown in FIG. 2, the Raman spectrum of the obtained sample showed a main peak at 1441 $cm^{-1}$, as well as peaks at 1924 $cm^{-1}$, 1279 $cm^{-1}$, 1066 $cm^{-1}$, 846 $cm^{-1}$, 772 $cm^{-1}$, and 481 $cm^{-1}$. The following are the relations of peak intensities: the peak intensity at 1924 $cm^{-1}$ was about 0.06 times the peak intensity at 1441 $cm^{-1}$; the peak intensity at 1279 $cm^{-1}$ was about 0.3 times the peak intensity at 1441 $cm^{-1}$; the peak intensity at 1066 $cm^{-1}$ was about 0.07 times the peak intensity at 1441 $cm^{-1}$; the peak intensity at 846 $cm^1$ was about 0.04 times the peak intensity at 1441 $cm^{-1}$; and the peak intensity at 481 $cm^{-1}$ was about 0.1 times the peak intensity at 1441 $cm^{-1}$. Conditions for Raman spectrum: an analyzer ALMEGA XR produced by Thermo Fisher Scientific; laser wavelength: 532 nm; slits: 50 µm; exposure: 5 seconds×12 times.

Figure 3:
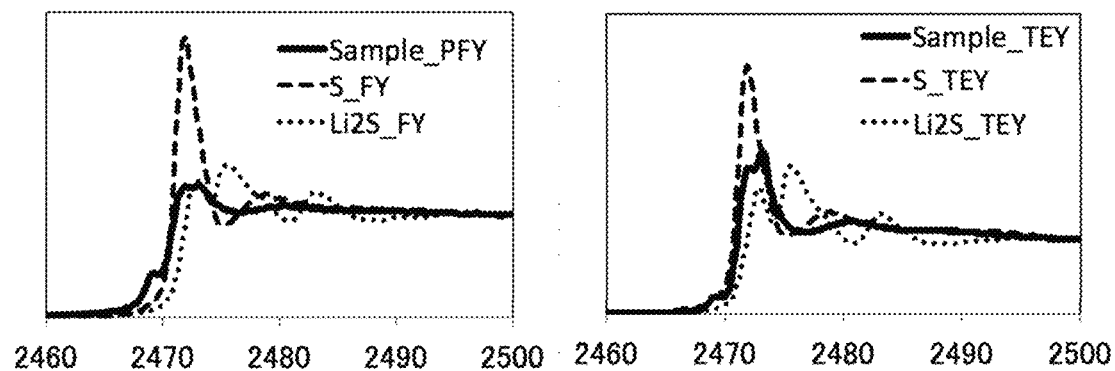
FIG. 3 is graphs showing XAFS spectra (2460-2500 eV) of the organic sulfur material obtained in Example 1. The figure on the left shows the partial fluorescence yield while the figure on the right shows the total electron yield. The sulfur and lithium sulfide spectra are also shown as a reference.

Further, as shown in FIG. 3, the XAFS spectrum showed intense absorption peaks at 2472.0 eV and 2473.2 eV, as well as an absorption peak at 2469.2 eV. In terms of the partial fluorescence yield, the following are the relations of peak intensities: the peak intensity at 2472.0 eV was about 3 times the peak intensity at 2469.2 eV, and the peak intensity at 2473.2 eV was about 3 times the peak intensity at 2469.2 eV. As can be understood from a comparison with the absorption peaks of sulfur and lithium sulfide shown in FIG. 3 as a reference, no absorption peaks of sulfur or lithium sulfide were confirmed in the organic sulfur material of Example 1, indicating no presence of free sulfur.

Figure 4:
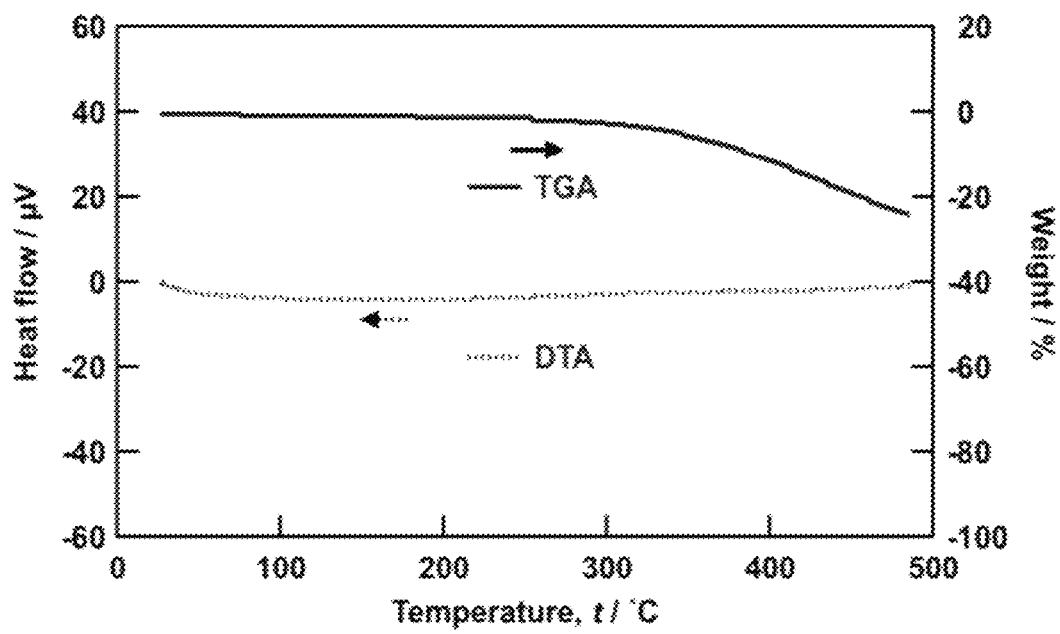
FIG. 4 is a graph showing TG-DTA curves (25-500° C.) of the organic sulfur material obtained in Example 1.

Furthermore, as shown in the TG-DTA curves in FIG. 4, the weight loss was not observed until at a temperature of about 300° C., which indicates that the organic sulfur material of Example 1 had excellent heat resistance and was a stable material.

Accordingly, an organic sulfur material containing a component that has undergone carbonization and having excellent heat resistance was obtained, the material having carbon and sulfur interactions.

Figure 5:
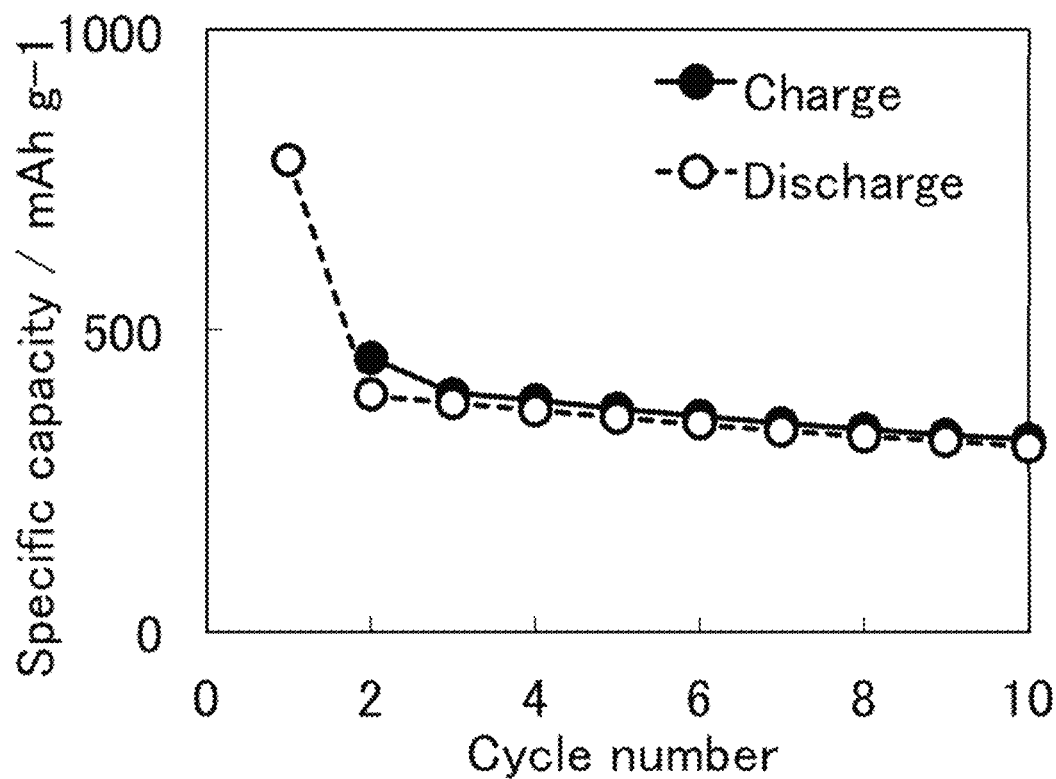
FIG. 5 is a graph showing the charge and discharge test results of the non-aqueous electrolyte lithium secondary battery obtained in Example 1.

The obtained organic sulfur material was used as a cathode active material and mixed in an agate mortar, such that the organic sulfur material:acetylene black:polytetrafluoroethylene (PTFE)=5:4:1 (weight ratio). The resulting mixture was compression-bonded to an aluminum mesh as a collector to thus obtain a cathode. Then, a charge and discharge test was conducted at a constant current mode of 0.05 C and at a cutoff voltage of 1.0 to 3.0 V by starting from discharge using a metal lithium as an anode, an electrolyte solution obtained by dissolving lithium trifluoromethanesulfonyl amide (LiTFSA) in tetraglyme at a molar ratio of 1:1, and a polypropylene film as a separator. FIG. 5 shows the charge and discharge characteristics. The initial discharge capacity was about 780 mAh/g, which was higher than that of the organic sulfur material, mentioned below, obtained using polyacrylonitrile (PAN) as a starting material (Comparative Example 1; about 720 mAh/g). Further, the initial charge capacity was about 450 mAh/g, which was higher than that of the organic sulfur material, mentioned below, obtained using polyacrylonitrile (PAN) as a starting material (Comparative Example 1; about 430 mAh/g).

The results indicate that the production of an organic sulfur material under the conditions adopted in the present invention and use of the organic sulfur material as a cathode active material of a non-aqueous electrolyte lithium secondary battery led the lithium secondary battery to have a high capacity.

Example 2

Large Volume Synthesis of Polyethylene Glycol 200

The synthesis of Example 1 was scaled up. Specifically, 51.6 g of sulfur (Kishida Chemical Co., Ltd., 99%) and 25.0 g of polyethylene glycol (Kishida Chemical Co., Ltd., average molecular weight: 190 to 210) were placed in an alumina pipe (diameter: 60 mm×length: 400 mm), and a silicone rubber stopper provided with a nitrogen gas inlet, a gas outlet, and an alumina protective tube (SSA-S, inner diameter: 2 mm, outer diameter: 4 mm, length: 500 mm) for inserting a thermocouple was attached (FIG. 1). The lower part of the test tube, 100 mm from the bottom, was placed in the heating portion of an electric furnace, a heat insulation material was inserted into the furnace to secure the test tube, and the upper part of the test tube was left exposed to open air. A thermocouple (type K) was inserted into the alumina protective tube, and the temperature of the sample was measured. Nitrogen gas was introduced at a rate of 50 mL per minute, and the exhaust gas was led to an Erlenmeyer flask containing 100 mL of 10% sodium hydroxide to collect hydrogen sulfide from the generated gas. The electric furnace set temperature was gradually increased to 500° C. over a period of 20 minutes. At 280° C., the sample temperature reached a plateau, and the generation of gas that was believed to be hydrogen sulfide was observed. Then, heating was performed over a period of 1 hour until the sample temperature reached 440° C. Subsequently, the furnace was turned on its side (rotated 90 degrees) to allow unreacted sulfur to be vaporized and removed from the reaction product. After cooling, the reaction product was collected from the test tube, crushed, passed through a sieve with openings having a size of 250 µm, and placed in a quartz boat, which was disposed inside a quartz tube (inner diameter: 30 mm, length: 900 mm) to allow sulfur to be vaporized and removed at 300° C. under nitrogen stream for 2 hours. In this manner, 8.888 g of black solid powder was obtained.

The thus obtained organic sulfur material was analyzed by Raman spectroscopy, XAFS spectroscopy, and TG-DTA, as in Example 1. The results were the same as those obtained in Example 1. Specifically, an organic sulfur material containing a component that has undergone carbonization and having excellent heat resistance was obtained, the material having carbon and sulfur interactions.

Figure 6:
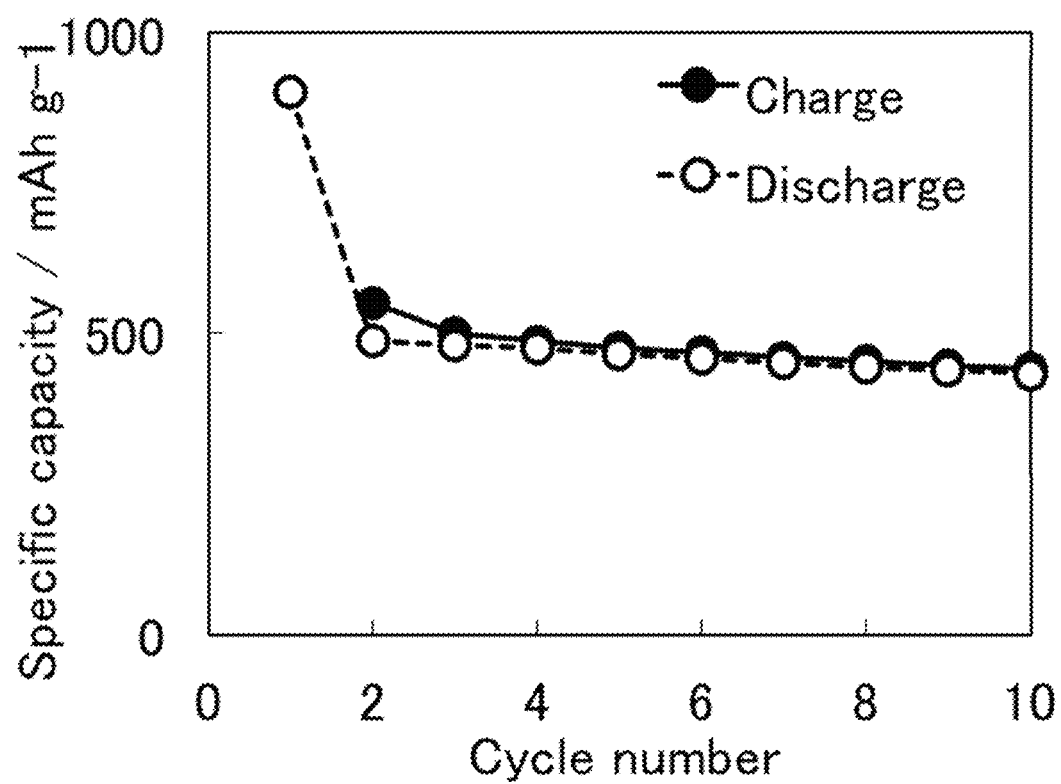
FIG. 6 is a graph showing the charge and discharge test results of the non-aqueous electrolyte lithium secondary battery obtained in Example 2.

The charge and discharge test was conducted in completely the same manner as in Example 1, except that this organic sulfur material was used as a cathode active material of a non-aqueous electrolyte lithium secondary battery. FIG. 6 shows the charge and discharge characteristics. The initial discharge capacity was about 910 mAh/g, which was higher than that of the organic sulfur material, mentioned below, obtained using polyacrylonitrile (PAN) as a starting material (Comparative Example 1; about 720 mAh/g). Further, the initial charge capacity was about 550 mAh/g, which was higher than that of the organic sulfur material, mentioned below, obtained using polyacrylonitrile (PAN) as a starting material (Comparative Example 1; about 430 mAh/g).

The results indicate that the production of an organic sulfur material under the conditions adopted in the present invention and use of the organic sulfur material as a cathode active material of a non-aqueous electrolyte lithium secondary battery led the lithium secondary battery to have a high capacity.

Comparative Example 1

Polyacrylonitrile

An organic sulfur material was produced by using completely the same method disclosed in NPL 3. Specifically, 5.2994 g of polyacrylonitrile (average molecular weight: 150000; Aldrich) crushed in a mortar, and 8.1194 g of sulfur (Kishida Chemical Co., Ltd., 99%) were mixed. The resulting mixture was placed on aluminum foil and heated under argon gas stream in a quartz tube horizontally disposed in an electric furnace until the sample temperature reached 350° C. The obtained reaction product was put on aluminum foil, which was disposed inside a quartz tube to vaporize and remove sulfur under a flow of argon at 280° C. for 2 hours. In this manner, 7.8687 g of black solid powder was obtained.

According to elemental analysis of the obtained sample performed using a device that simultaneously quantifies carbon, hydrogen, and nitrogen, an O micro corder, and ion chromatography, the carbon content was 39.2 wt %, the hydrogen content was 1.0 wt %, the oxygen content was 2.9 wt %, the sulfur content was 43.1 wt %, and the nitrogen content was 13.8 wt %.

Figure 7:
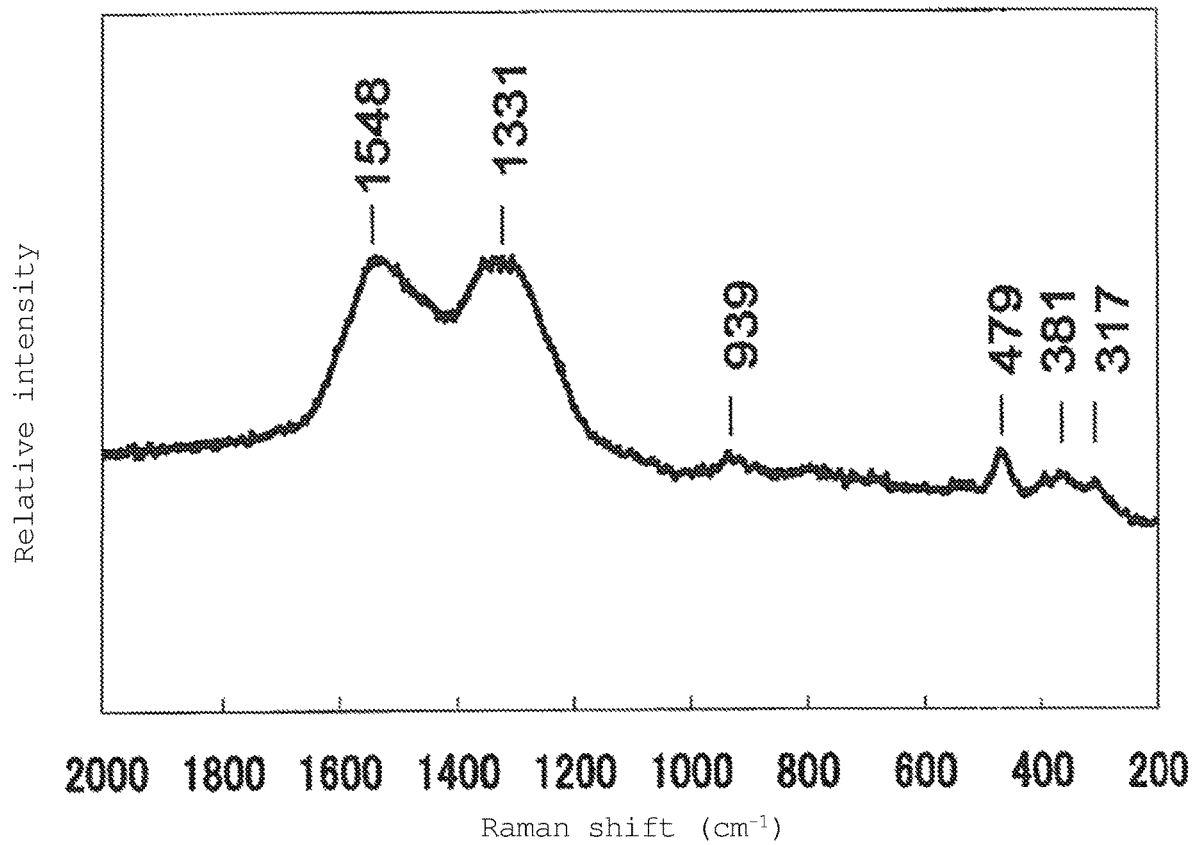
FIG. 7 is a graph showing a Raman spectrum (200-2000 cm$^{-1}$) of the organic sulfur material obtained in Comparative Example 1.

As shown in FIG. 7, the Raman spectrum of the obtained sample showed intense peaks at 1331 cm$^{-1}$ and 1548 cm$^{-1}$, as well as peaks at 939 cm$^{-1}$, 479 cm$^{-1}$, 381 cm$^{-1}$, and 317 cm$^{-1}$, which indicates that the sample was a material completely different from those of Examples 1 and 2.

Figure 8:
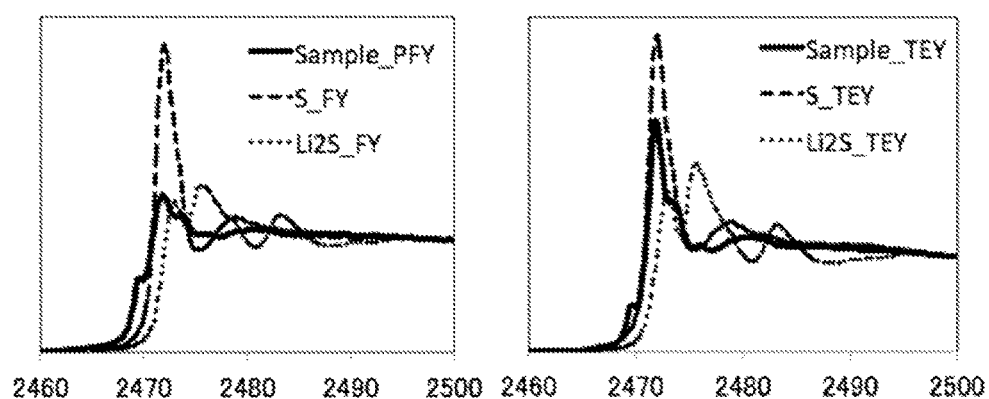
FIG. 8 is graphs showing XAFS spectra (2460-2500 eV) of the organic sulfur material obtained in Comparative Example 1. The figure on the left shows the partial fluorescence yield while the figure on the right shows the total electron yield. The sulfur and lithium sulfide spectra are also shown as a reference.

Further, as shown in FIG. 8, the XAFS spectrum showed the most intense absorption peak at 2471.7 eV, which indicates that the sample was a material completely different from those of Examples 1 and 2.

Figure 9:
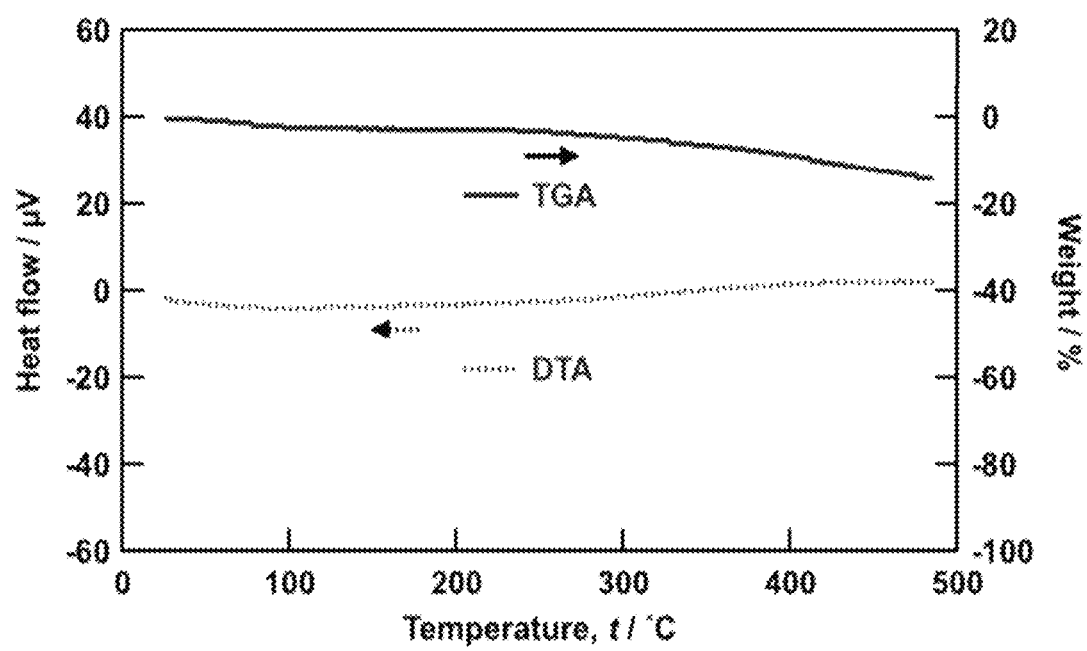
FIG. 9 is a graph showing TG-DTA curves (25-500° C.) of the organic sulfur material obtained in Comparative Example 1.

Furthermore, as shown in the TG-DTA curves in FIG. 9, the weight was gradually decreased at a temperature of 50° C. or higher, which indicates the removal of sulfur. This suggests that the organic sulfur material of Comparative Example 1 contained a considerable amount of free sulfur, unlike Example 1 or 2.

The above results confirm that the target organic sulfur material cannot be produced when polyethylene glycol or a derivative thereof is not used as a starting material.

Figure 10:
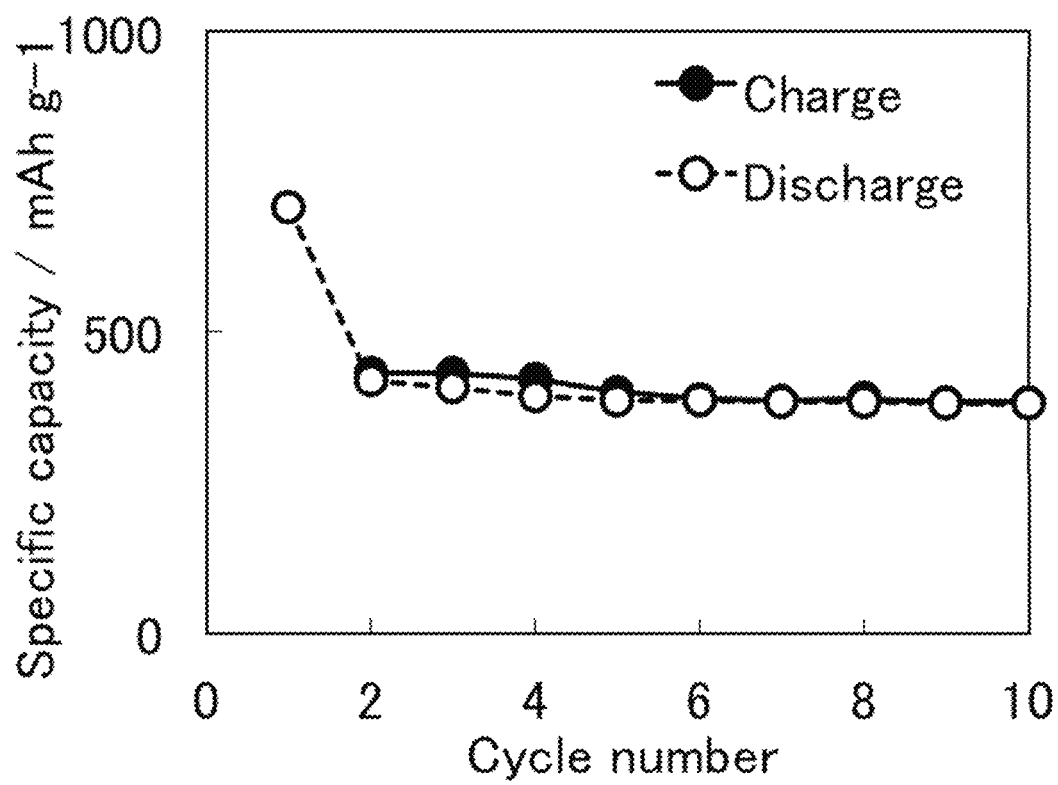
FIG. 10 is a graph showing the charge and discharge test results of the non-aqueous electrolyte lithium secondary battery obtained in Comparative Example 1.

The charge and discharge test was conducted in completely the same manner as in Example 1, except that this organic sulfur material was used as a cathode active material of a non-aqueous electrolyte lithium secondary battery. FIG. 10 shows the charge and discharge characteristics. The initial discharge capacity was about 720 mAh/g, which was lower than those of Examples 1 to 2. Further, the initial charge capacity was about 430 mAh/g, which was also lower than those of Examples 1 to 2.

Example 3

Polyethylene Glycol 300

As in Example 1, 7.6441 g of sulfur and 3.0437 g of polyethylene glycol 300 (Kishida Chemical Co., Ltd., average molecular weight: 300) were placed in a test tube, and heating was performed in an electric furnace under nitrogen stream for 1 hour until the sample temperature reached 436° C. The obtained reaction product was put in a quartz boat, which was disposed inside a quartz tube to vaporize and remove sulfur under a flow of nitrogen at 300° C. for 2 hours. In this manner, 0.7263 g of black solid powder was obtained.

The thus obtained organic sulfur material was analyzed by Raman spectroscopy, XAFS spectroscopy, and TG-DTA, as in Example 1. The results were the same as those obtained in Example 1. Specifically, an organic sulfur material containing a component that has undergone carbonization and having excellent heat resistance was obtained, the material having carbon and sulfur interactions.

Figure 11:
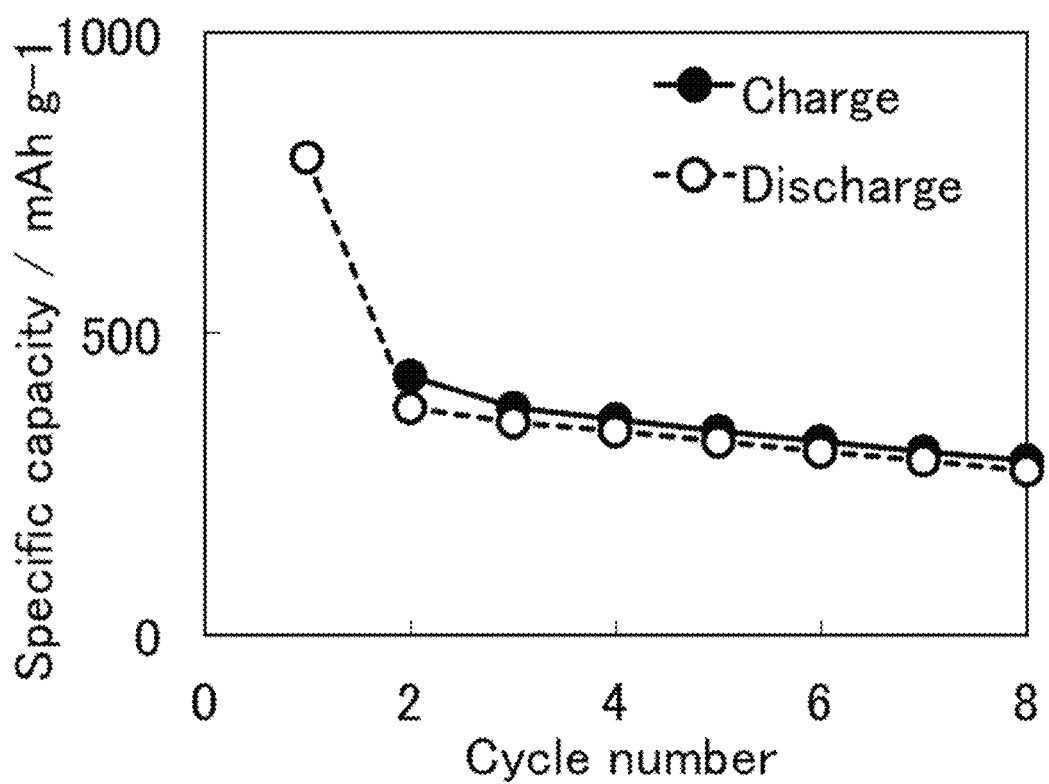
FIG. 11 is a graph showing the charge and discharge test results of the non-aqueous electrolyte lithium secondary battery obtained in Example 3.

The charge and discharge test was conducted in completely the same manner as in Example 1, except that this organic sulfur material was used as a cathode active material of a non-aqueous electrolyte lithium secondary battery. FIG. 11 shows the charge and discharge characteristics. The initial discharge capacity was about 792 mAh/g, which was higher than that of the organic sulfur material obtained using polyacrylonitrile (PAN) as a starting material (Comparative Example 1; about 720 mAh/g). Further, the initial charge capacity was about 430 mAh/g, which was comparable to that of the organic sulfur material obtained using polyacrylonitrile (PAN) as a starting material (Comparative Example 1; about 430 mAh/g).

The results indicate that the production of an organic sulfur material under the conditions adopted in the present invention and use of the organic sulfur material as a cathode active material of a non-aqueous electrolyte lithium secondary battery led the lithium secondary battery to have a high capacity.

Example 4

Polyethylene Glycol 600

As in Example 1, 8.4770 g of sulfur and 3.3982 g of polyethylene glycol 600 (Kishida Chemical Co., Ltd., average molecular weight: 600) were placed in a test tube, and heating was performed in an electric furnace under nitrogen stream for 1 hour until the sample temperature reached 426° C. The obtained reaction product was put in a quartz boat, which was disposed inside a quartz tube to vaporize and remove sulfur under a flow of nitrogen at 300° C. for 2 hours. In this manner, 1.0060 g of black solid powder was obtained.

The thus obtained organic sulfur material was analyzed by Raman spectroscopy, XAFS spectroscopy, and TG-DTA, as in Example 1. The results were the same as those obtained in Example 1. Specifically, an organic sulfur material containing a component that has undergone carbonization and having excellent heat resistance was obtained, the material having carbon and sulfur interactions.

Figure 12:
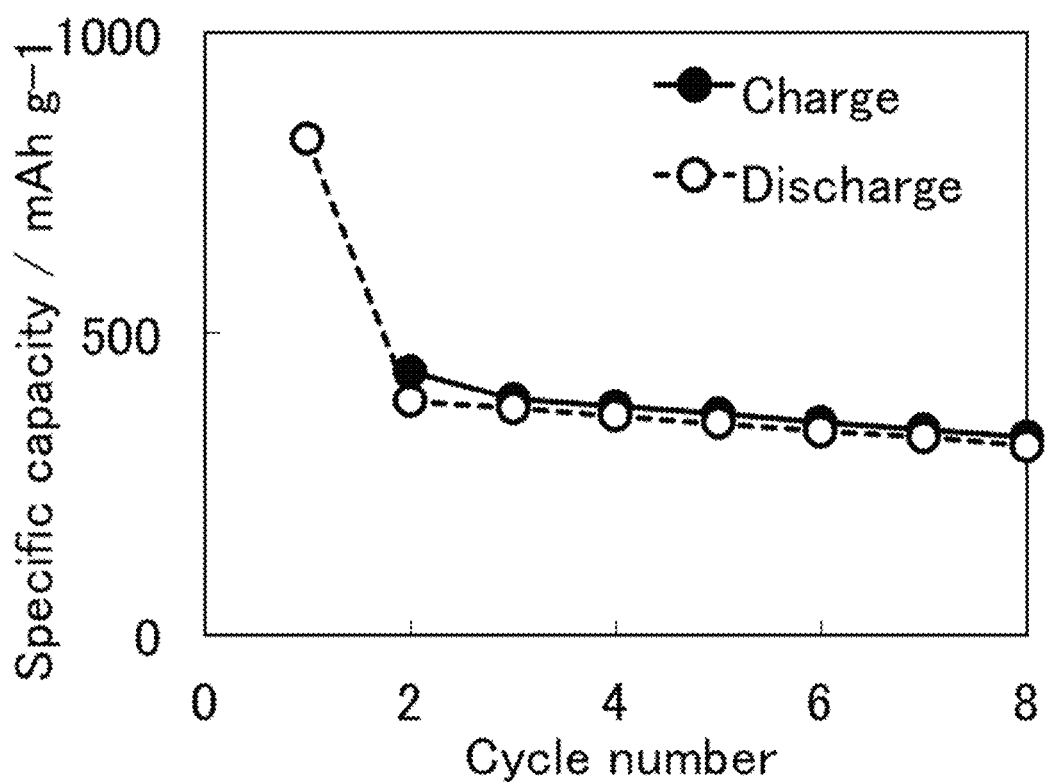
FIG. 12 is a graph showing the charge and discharge test results of the non-aqueous electrolyte lithium secondary battery obtained in Example 4.

The charge and discharge test was conducted in completely the same manner as in Example 1, except that this organic sulfur material was used as a cathode active material of a non-aqueous electrolyte lithium secondary battery. FIG. 12 shows the charge and discharge characteristics. The initial discharge capacity was about 824 mAh/g, which was higher than that of the organic sulfur material obtained using polyacrylonitrile (PAN) as a starting material (Comparative Example 1; about 720 mAh/g). Further, the initial charge capacity was about 437 mAh/g, which was higher than that of the organic sulfur material obtained using polyacrylonitrile (PAN) as a starting material (Comparative Example 1; about 430 mAh/g).

The results indicate that the production of an organic sulfur material under the conditions adopted in the present invention and use of the organic sulfur material as a cathode active material of a non-aqueous electrolyte lithium secondary battery led the lithium secondary battery to have a high capacity.

Example 5

Tetraglyme

As in Example 1, 4.0848 g of sulfur and 1.5211 g of tetraglyme (Kishida Chemical Co., Ltd.) were placed in a test tube, and heating was performed in an electric furnace under nitrogen stream for 1 hour until the sample temperature reached 454° C. The obtained reaction product was put in a quartz boat, which was disposed inside a quartz tube to vaporize and remove sulfur under a flow of nitrogen at 300° C. for 2 hours. In this manner, 0.1103 g of black solid powder was obtained.

According to elemental analysis of the obtained sample performed using a device that simultaneously quantifies carbon, hydrogen, and nitrogen, an O micro corder, and ion chromatography, the carbon content was 37.8 wt %, the hydrogen content was 0.5 wt %, the oxygen content was 3.1 wt %, the sulfur content was 58.6 wt %, and the nitrogen content was 0.0 wt % (not present).

Figure 13:
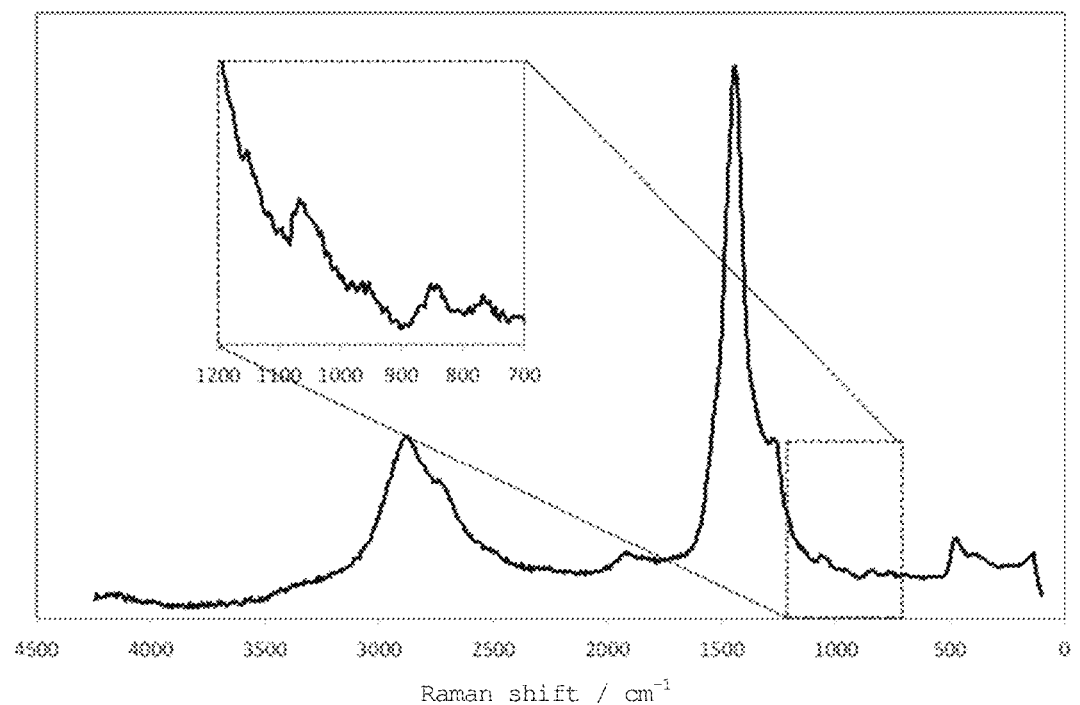
FIG. 13 is a graph showing a Raman spectrum (100-4250 $cm^{-1}$) of the organic sulfur material obtained in Example 5.

As shown in FIG. 13, the Raman spectrum of the obtained sample showed a main peak at 1441 cm$^{-1}$, as well as peaks at 1931 cm$^{-1}$, 1268 cm$^{-1}$, 1067 cm$^{-1}$, 838 cm$^{-1}$, 770 cm$^{-1}$, and 481 cm$^{-1}$. The following are the relations of peak intensities: the peak intensity at 1931 cm$^{-1}$ was about 0.1 times the peak intensity at 1441 cm$^{-1}$, the peak intensity at 1268 cm$^{-1}$ was about 0.3 times the peak intensity at 1441 cm$^{-1}$, the peak intensity at 1067 cm$^{-1}$ was about 0.1 times the peak intensity at 1441 cm$^{-1}$, the peak intensity at 838 cm$^1$ was about 0.09 times the peak intensity at 1441 cm$^{-1}$, the peak intensity at 770 cm$^{-1}$ was about 0.08 times the peak intensity at 1441 cm$^{-1}$, and the peak intensity at 481 cm$^{-1}$ was about 0.1 times the peak intensity at 1441 cm$^{-1}$.

Figure 14:
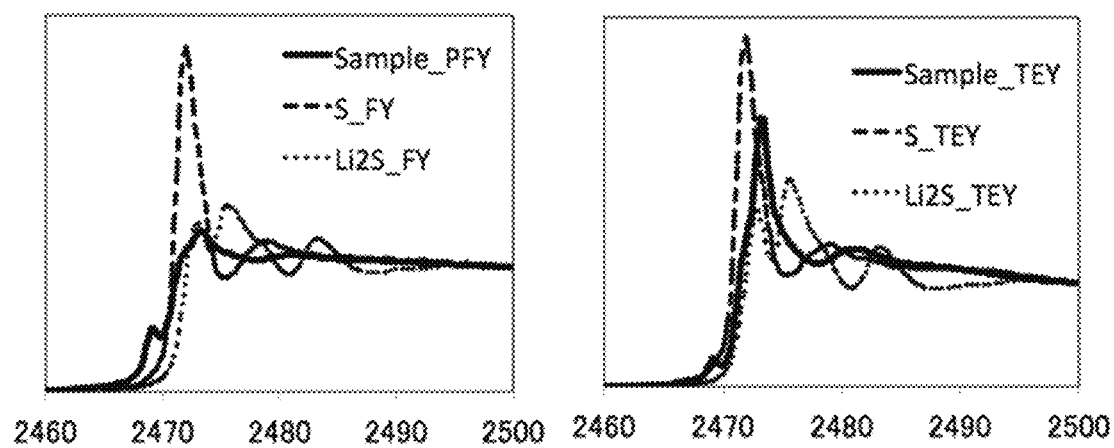
FIG. 14 is graphs showing XAFS spectra (2460-2500 eV) of the organic sulfur material obtained in Example 5. The figure on the left shows the partial fluorescence yield while the figure on the right shows the total electron yield. The sulfur and lithium sulfide spectra are also shown as a reference.

Further, as shown in FIG. 14, the XAFS spectrum showed intense absorption peaks at 2472.0 eV and 2473.2 eV, as well as an absorption peak at 2469.2 eV. In terms of the partial fluorescence yield, the following are the relations of peak intensities: the peak intensity at 2472.0 eV was about 3 times the peak intensity at 2469.2 eV, and the peak intensity at 2473.2 eV was about 3 times the peak intensity at 2469.2 eV. As can be understood from a comparison with the absorption peaks of sulfur and lithium sulfide shown in FIG. 14 as a reference, no absorption peaks of sulfur or lithium sulfide were confirmed in the organic sulfur material of Example 5, indicating no presence of free sulfur.

Accordingly, an organic sulfur material containing a component that has undergone carbonization was obtained, the material having carbon and sulfur interactions.

The charge and discharge test was conducted in completely the same manner as in Example 1, except that this organic sulfur material was used as a cathode active material of a non-aqueous electrolyte lithium secondary battery. The results were the same as those obtained in Example 1, which indicates that the production of an organic sulfur material under the conditions adopted in the present invention and use of the organic sulfur material as a cathode active material of a non-aqueous electrolyte lithium secondary battery led the lithium secondary battery to have a high capacity.

Example 6

Large-Volume Synthesis of Tetraglyme

As in Example 2, 51.2155 g of sulfur and 24.8068 g of tetraglyme (Kishida Chemical Co., Ltd.) were placed in a test tube, and heating was performed in an electric furnace under nitrogen stream for 1 hour until the sample temperature reached 457° C. The obtained reaction product was put in a quartz boat, which was disposed inside a quartz tube to vaporize and remove sulfur under a flow of nitrogen at 300° C. for 2 hours. In this manner, 6.7746 g of black solid powder was obtained.

The thus obtained organic sulfur material was analyzed by Raman spectroscopy, XAFS spectroscopy, and TG-DTA, as in Example 1. The results were the same as those obtained in Example 1. Specifically, an organic sulfur material containing a component that has undergone carbonization and having excellent heat resistance was obtained, the material having carbon and sulfur interactions.

Figure 15:
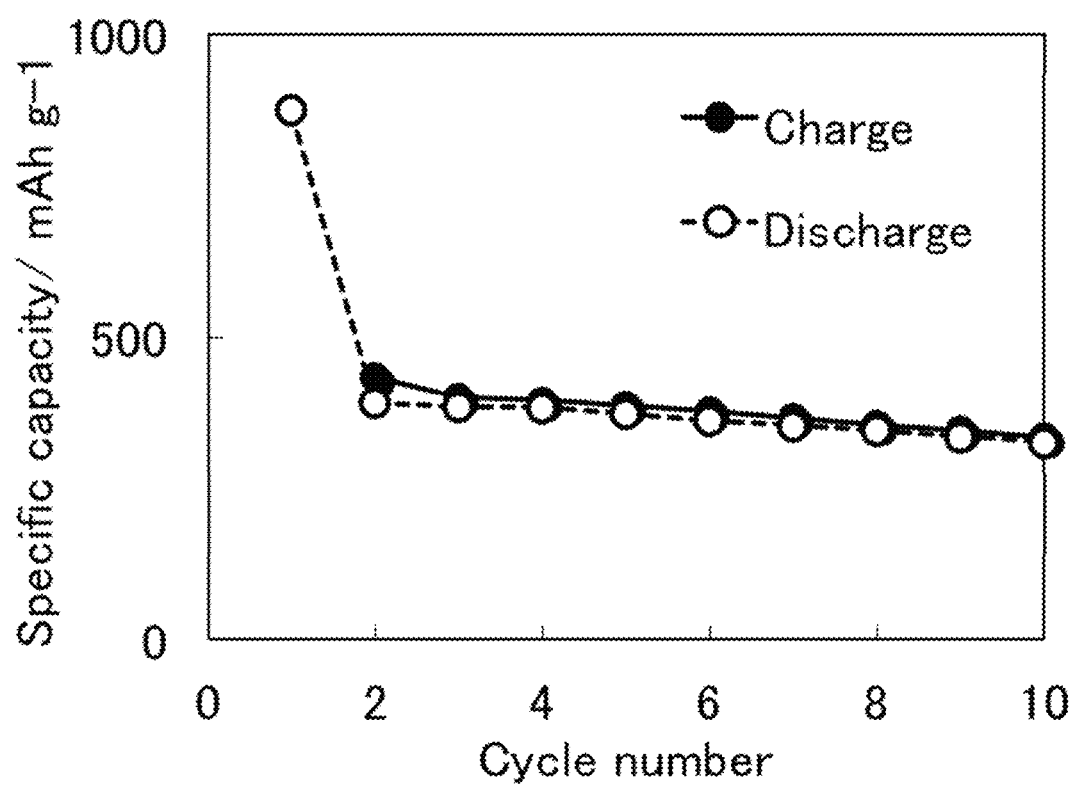
FIG. 15 is a graph showing the charge and discharge test results of the non-aqueous electrolyte lithium secondary battery obtained in Example 6.

The charge and discharge test was conducted in completely the same manner as in Example 1, except that this organic sulfur material was used as a cathode active material of a non-aqueous electrolyte lithium secondary battery. FIG. 15 shows the charge and discharge characteristics. The initial discharge capacity was about 870 mAh/g, which was higher than that of the organic sulfur material obtained using polyacrylonitrile as a starting material (Comparative Example 1; about 720 mAh/g). Further, the initial charge capacity was about 440 mAh/g, which was higher than that of the organic sulfur material obtained using polyacrylonitrile as a starting material (Comparative Example 1; about 430 mAh/g).

The results indicate that the production of an organic sulfur material under the conditions adopted in the present invention and use of the organic sulfur material as a cathode active material of a non-aqueous electrolyte lithium secondary battery led the lithium secondary battery to have a high capacity.

Example 7

Polyethylene Glycol 6000

As in Example 1, 5.5001 g of sulfur and 1.3932 g of polyethylene glycol 6000 (Kishida Chemical Co., Ltd., average molecular weight: 6000) were placed in a test tube, and heating was performed in an electric furnace under nitrogen stream for 1 hour until the sample temperature reached 427° C. The obtained reaction product was put in a quartz boat, which was disposed inside a quartz tube to vaporize and remove sulfur under a flow of nitrogen at 300° C. for 4 hours. In this manner, 0.0971 g of black solid powder was obtained.

For the thus obtained organic sulfur material, Raman spectroscopy, XAFS spectroscopy, TG-DTA, and charge and discharge measurement were performed as in Example 1. The results were the same as those obtained in Example 1. Specifically, an organic sulfur material containing a component that has undergone carbonization and having excellent heat resistance and high capacity was obtained, the material having carbon and sulfur interactions.

Example 8

Polyethylene Glycol 1540

As in Example 1, 6.0186 g of sulfur and 2.2894 g of polyethylene glycol 1540 (Kishida Chemical Co., Ltd., average molecular weight: 1540) were placed in a test tube, and heating was performed in an electric furnace under nitrogen stream for 1 hour until the sample temperature reached 428° C. The obtained reaction product was put in a quartz boat, which was disposed inside a quartz tube to vaporize and remove sulfur under a flow of nitrogen at 300° C. for 2 hours. In this manner, 0.7280 g of black solid powder was obtained.

For the thus obtained organic sulfur material, Raman spectroscopy, XAFS spectroscopy, TG-DTA, and charge and discharge measurement were performed as in Example 1. The results were the same as those obtained in Example 1. Specifically, an organic sulfur material containing a component that has undergone carbonization and having excellent heat resistance and high capacity was obtained, the material having carbon and sulfur interactions.

Example 9

Polyethylene Glycol 400

As in Example 1, 8.8828 g of sulfur and 3.5158 g of polyethylene glycol 400 (Kishida Chemical Co., Ltd., average molecular weight: 400) were placed in a test tube, and heating was performed in an electric furnace under nitrogen stream for 1 hour until the sample temperature reached 439° C. The obtained reaction product was put in a quartz boat, which was disposed inside a quartz tube to vaporize and remove sulfur under a flow of nitrogen at 300° C. for 1 hour. In this manner, 0.9762 g of black solid powder was obtained.

The thus obtained organic sulfur material was analyzed by Raman spectroscopy, XAFS spectroscopy, and TG-DTA, as in Example 1. The results were the same as those obtained in Example 1. Specifically, an organic sulfur material containing a component that has undergone carbonization and having excellent heat resistance was obtained, the material having carbon and sulfur interactions.

Figure 16:
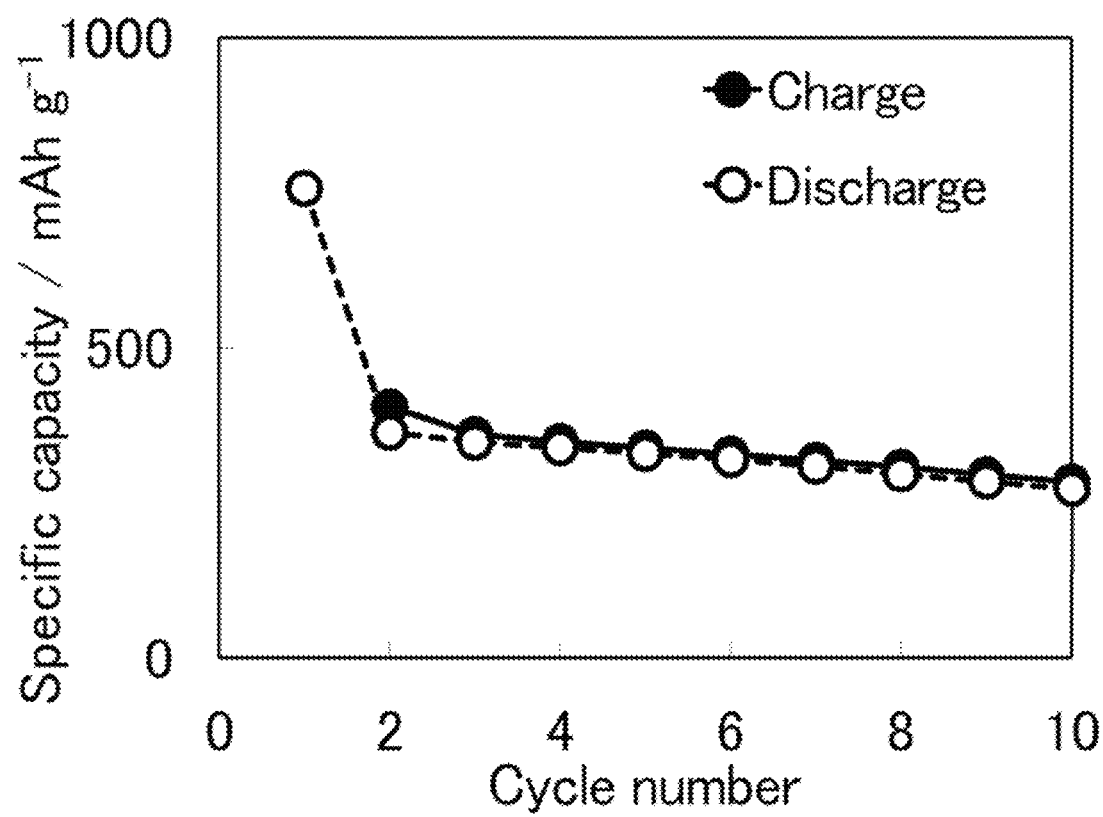
FIG. 16 is a graph showing the charge and discharge test results of the non-aqueous electrolyte lithium secondary battery obtained in Example 9.

The charge and discharge test was conducted in completely the same manner as in Example 1, except that this organic sulfur material was used as a cathode active material of a non-aqueous electrolyte lithium secondary battery. FIG. 16 shows the charge and discharge characteristics. The initial discharge capacity was about 760 mAh/g, which was higher than that of the organic sulfur material obtained using polyacrylonitrile (PAN) as a starting material (Comparative Example 1; about 720 mAh/g).

Example 10

Polyethylene Glycol 1000

As in Example 1, 8.1878 g of sulfur and 3.0762 g of polyethylene glycol 1000 (Kishida Chemical Co., Ltd., average molecular weight: 1000) were placed in a test tube, and heating was performed in an electric furnace under nitrogen stream for 1 hour until the sample temperature reached 438° C. The obtained reaction product was put in a quartz boat, which was disposed inside a quartz tube to vaporize and remove sulfur under a flow of nitrogen at 300° C. for 2 hours. In this manner, 1.0672 g of black solid powder was obtained.

The thus obtained organic sulfur material was analyzed by Raman spectroscopy, XAFS spectroscopy, and TG-DTA, as in Example 1. The results were the same as those obtained in Example 1. Specifically, an organic sulfur material containing a component that has undergone carbonization and having excellent heat resistance was obtained, the material having carbon and sulfur interactions.

Example 11

Polyethylene Glycol 2000

As in Example 1, 4.6656 g of sulfur and 1.2115 g of polyethylene glycol 2000 (Kishida Chemical Co., Ltd., average molecular weight: 2000) were placed in a test tube, and heating was performed in an electric furnace under nitrogen stream for 1 hour until the sample temperature reached 438° C. The obtained reaction product was put in a quartz boat, which was disposed inside a quartz tube to vaporize and remove sulfur under a flow of nitrogen at 300° C. for 2 hours. In this manner, 0.2854 g of black solid powder was obtained.

For the thus obtained organic sulfur material, Raman spectroscopy, XAFS spectroscopy, TG-DTA, and charge and discharge measurement were performed as in Example 1. The results were the same as those obtained in Example 1. Specifically, an organic sulfur material containing a component that has undergone carbonization and having excellent heat resistance and high capacity was obtained, the material having carbon and sulfur interactions.

Example 12

Polyethylene Glycol 4000

As in Example 1, 4.7693 g of sulfur and 1.3251 g of polyethylene glycol 4000 (Kishida Chemical Co., Ltd., average molecular weight: 4000) were placed in a test tube, and heating was performed in an electric furnace under nitrogen stream for 1 hour until the sample temperature reached 427° C. The obtained reaction product was put in a quartz boat, which was disposed inside a quartz tube to vaporize and remove sulfur under a flow of nitrogen at 300° C. for 2 hours. In this manner, 0.4522 g of black solid powder was obtained.

The thus obtained organic sulfur material was analyzed by Raman spectroscopy, XAFS spectroscopy, and TG-DTA, as in Example 1. The results were the same as those obtained in Example 1. Specifically, an organic sulfur material containing a component that has undergone carbonization and having excellent heat resistance was obtained, the material having carbon and sulfur interactions.

Figure 17:
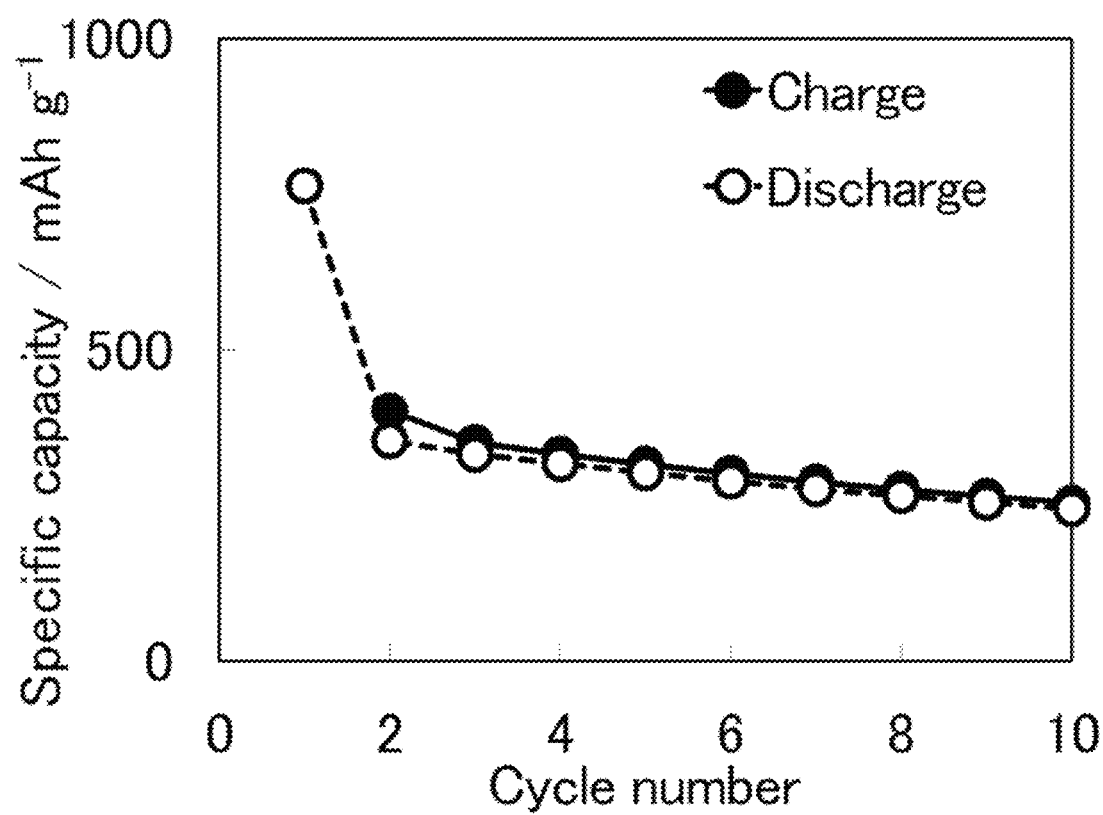
FIG. 17 is a graph showing the charge and discharge test results of the non-aqueous electrolyte lithium secondary battery obtained in Example 12.

The charge and discharge test was conducted in completely the same manner as in Example 1, except that this organic sulfur material was used as a cathode active material of a non-aqueous electrolyte lithium secondary battery. FIG. 17 shows the charge and discharge characteristics. The initial discharge capacity was about 760 mAh/g, which was higher than that of the organic sulfur material obtained using polyacrylonitrile (PAN) as a starting material (Comparative Example 1; about 720 mAh/g).

Example 13

Large-Volume Synthesis of Polyethylene Glycol 4000

The synthesis of Example 12 was scaled up. Specifically, the synthesis was performed as follows. Sulfur (Hosoi Chemical Industry Co., Ltd.; 99.9%) (390.0 g) and 276.0 g of polyethylene glycol 4000 (Kishida Chemical Co., Ltd., average molecular weight: 4000) were placed in a mullite tube, which was put in a stainless steel container, to which a stainless steel lid provided with a nitrogen gas inlet, a gas outlet, and an alumina protective tube for inserting a thermocouple was attached. The lower part of the stainless steel container was placed in the heating portion of an electric furnace and heated, a heat insulation material was inserted into the furnace to secure the container, and the upper part of the container was left exposed to open air. A thermocouple was inserted into the alumina protective tube, and the temperature of the sample was measured. Nitrogen gas was introduced at a rate of 100 mL per minute, and the exhaust gas was led to an Erlenmeyer flask containing 10% sodium hydroxide to collect hydrogen sulfide from the generated gas. The electric furnace set temperature was gradually increased to 500° C. At 255° C., the sample temperature reached a plateau, and the generation of gas that was believed to be hydrogen sulfide was observed. Then, heating was performed over a period of 5 hours until the sample temperature reached 274° C. After cooling, the reaction product was collected from the test tube, crushed, passed through a sieve with openings having a size of 250 μm, and placed in a quartz boat, which was disposed inside a quartz tube (inner diameter: 30 mm, length: 900 mm) to allow sulfur to be vaporized and removed at 400° C. for 1 hour under nitrogen stream. In this manner, 112.2 g of black solid powder was obtained.

The thus obtained organic sulfur material was analyzed by Raman spectroscopy, XAFS spectroscopy, and TG-DTA, as in Example 1. The results were the same as those obtained in Example 1. Specifically, an organic sulfur material containing a component that has undergone carbonization and having excellent heat resistance was obtained, the material having carbon and sulfur interactions.

Figure 18:
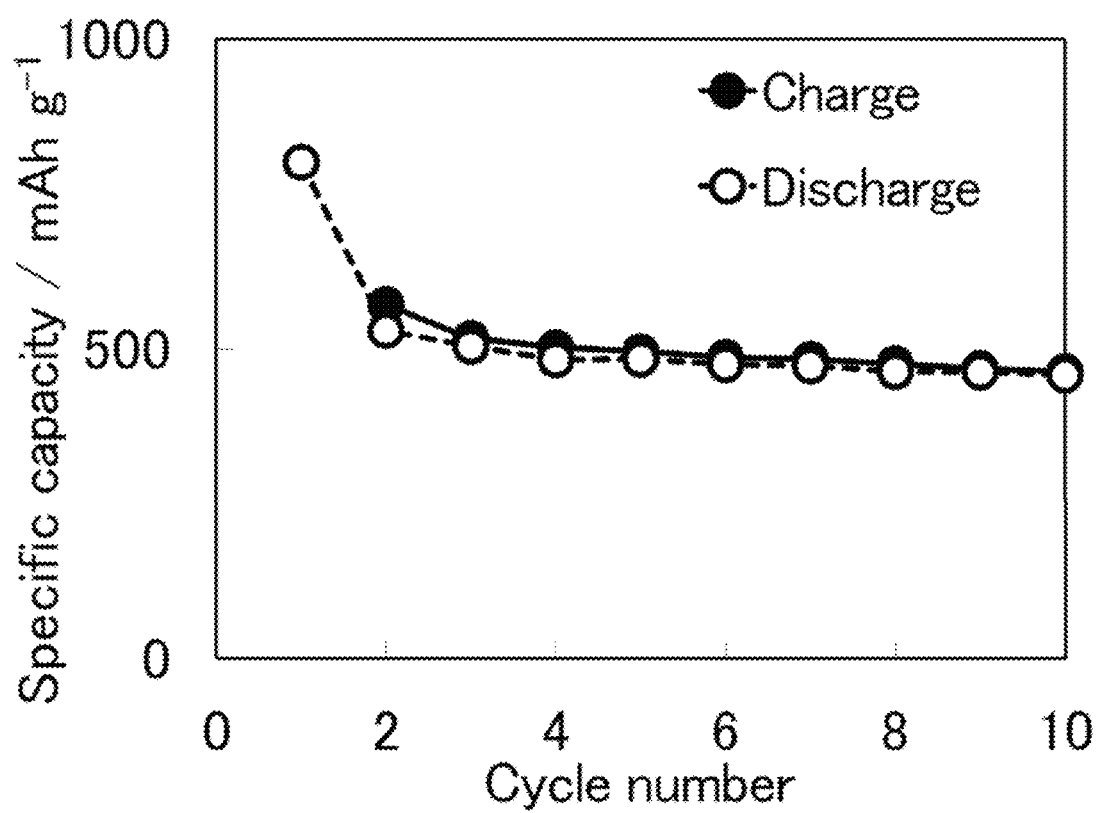
FIG. 18 is a graph showing the charge and discharge test results of the non-aqueous electrolyte lithium secondary battery obtained in Example 13.

The charge and discharge test was conducted in completely the same manner as in Example 1, except that this organic sulfur material was used as a cathode active material of a non-aqueous electrolyte lithium secondary battery. FIG. 18 shows the charge and discharge characteristics. The initial discharge capacity was about 800 mAh/g, which was higher than that of the organic sulfur material obtained using polyacrylonitrile (PAN) as a starting material (Comparative Example 1; about 720 mAh/g). Further, the initial charge capacity was about 570 mAh/g, which was higher than that of the organic sulfur material obtained using polyacrylonitrile (PAN) as a starting material (Comparative Example 1; about 430 mAh/g).

The results indicate that the production of an organic sulfur material under the conditions adopted in the present invention and use of the organic sulfur material as a cathode active material of a non-aqueous electrolyte lithium secondary battery led the lithium secondary battery to have a high capacity.

Example 14

Large-Volume Synthesis of Polyethylene Glycol 6000

The synthesis of Example 7 was scaled up. Specifically, the synthesis was performed as follows. Sulfur (Hosoi Chemical Industry Co., Ltd.; 99.9%) (325.0 g) and 230.2 g of polyethylene glycol 6000 (Kishida Chemical Co., Ltd., average molecular weight: 6000) were placed in a mullite tube, which was put in a stainless steel container, to which a stainless steel lid provided with a nitrogen gas inlet, a gas outlet, and an alumina protective tube for inserting a thermocouple was attached. The lower part of the stainless steel container was placed in the heating portion of an electric furnace and heated, a heat insulation material was inserted into the furnace to secure the container, and the upper part of the container was left exposed to open air. A thermocouple (type K) was inserted into the alumina protective tube, and the temperature of the sample was measured. Nitrogen gas was introduced, and the exhaust gas was led to an Erlenmeyer flask containing 10% sodium hydroxide to collect hydrogen sulfide from the generated gas. The electric furnace set temperature was gradually increased to 330° C. over a period of 120 minutes. At 247° C., the sample temperature reached a plateau, and the generation of gas that was believed to be hydrogen sulfide was observed. Then, heating was performed over a period of 5 hours until the sample temperature reached 288° C. After cooling, the reaction product was collected from the test tube, crushed, passed through a sieve with openings having a size of 250 µm, and placed in a quartz boat, which was disposed inside a quartz tube (inner diameter: 30 mm, length: 900 mm) to allow sulfur to be vaporized and removed under nitrogen stream at 400° C. for 3 hours. In this manner, 55.2 g of black solid powder was obtained.

The thus obtained organic sulfur material was analyzed by Raman spectroscopy, XAFS spectroscopy, and TG-DTA, as in Example 1. The results were the same as those obtained in Example 1. Specifically, an organic sulfur material containing a component that has undergone carbonization and having excellent heat resistance was obtained, the material having carbon and sulfur interactions.

Figure 19:
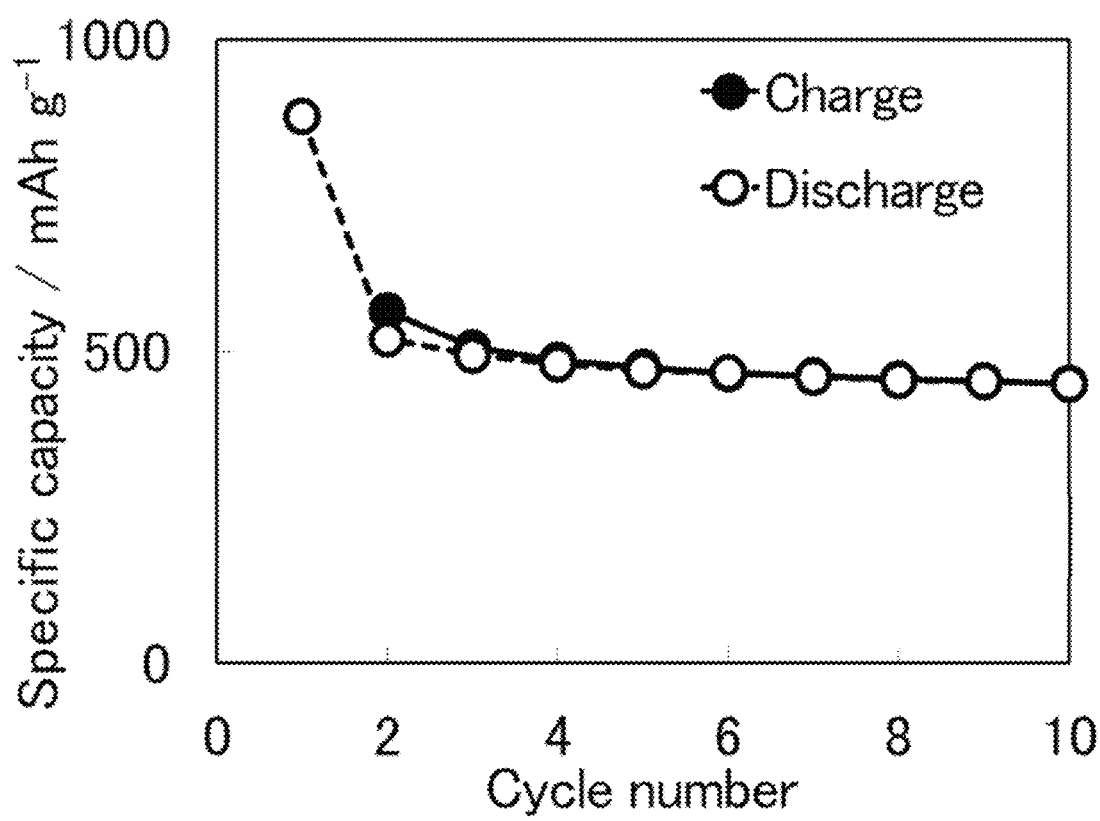
FIG. 19 is a graph showing the charge and discharge test results of the non-aqueous electrolyte lithium secondary battery obtained in Example 14.

The charge and discharge test was conducted in completely the same manner as in Example 1, except that this organic sulfur material was used as a cathode active material of a non-aqueous electrolyte lithium secondary battery. FIG. 19 shows the charge and discharge characteristics. The initial discharge capacity was about 870 mAh/g, which was higher than that of the organic sulfur material obtained using polyacrylonitrile (PAN) as a starting material (Comparative Example 1; about 720 mAh/g). Further, the initial charge capacity was about 560 mAh/g, which was higher than that of the organic sulfur material obtained using polyacrylonitrile (PAN) as a starting material (Comparative Example 1; about 430 mAh/g).

The results indicate that the production of an organic sulfur material under the conditions adopted in the present invention and use of the organic sulfur material as a cathode active material of a non-aqueous electrolyte lithium secondary battery led the lithium secondary battery to have a high capacity.

Example 15

Triglyme

As in Example 1, 3.9896 g of sulfur (Kishida Chemical Co., Ltd.; 99%), and 2.9633 g of triethylene glycol dimethyl ether (triglyme; Kishida Chemical Co., Ltd.) were placed in a test tube, and heating was performed in an electric furnace under nitrogen stream for 1 hour until the sample temperature reached 375° C. The obtained reaction product was put in a quartz boat, which was disposed inside a quartz tube to vaporize and remove sulfur under a flow of nitrogen at 300° C. for 4 hours. In this manner, 0.0142 g of black solid powder was obtained.

The thus obtained organic sulfur material was analyzed by Raman spectroscopy, XAFS spectroscopy, and TG-DTA, as in Example 1. The results were the same as those obtained in Example 1. Specifically, an organic sulfur material containing a component that has undergone carbonization and having excellent heat resistance was obtained, the material having carbon and sulfur interactions.

Figure 20:
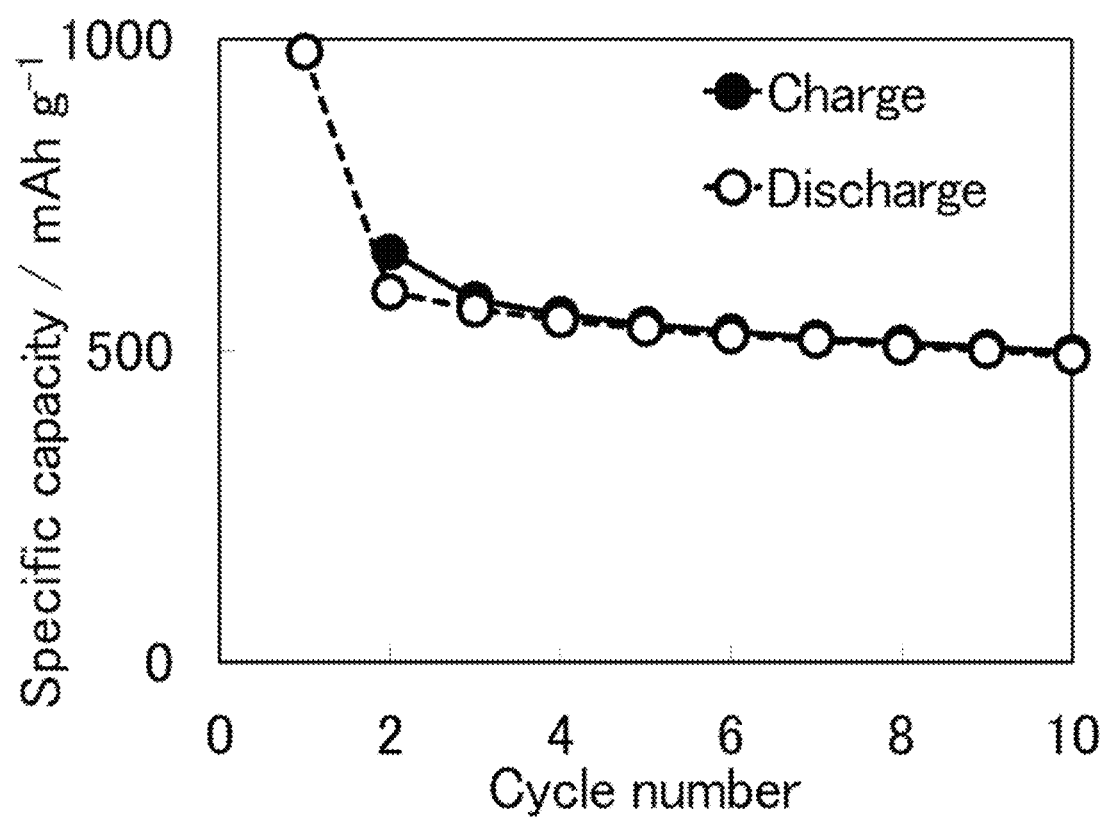
FIG. 20 is a graph showing the charge and discharge test results of the non-aqueous electrolyte lithium secondary battery obtained in Example 15.

The charge and discharge test was conducted in completely the same manner as in Example 1, except that this organic sulfur material was used as a cathode active material of a non-aqueous electrolyte lithium secondary battery. FIG. 20 shows the charge and discharge characteristics. The initial discharge capacity was about 980 mAh/g, which was higher than that of the organic sulfur material obtained using polyacrylonitrile (PAN) as a starting material (Comparative Example 1; about 720 mAh/g). Further, the initial charge capacity was about 650 mAh/g, which was higher than that of the organic sulfur material obtained using polyacrylonitrile (PAN) as a starting material (Comparative Example 1; about 430 mAh/g).

The results indicate that the production of an organic sulfur material under the conditions adopted in the present invention and use of the organic sulfur material as a cathode active material of a non-aqueous electrolyte lithium secondary battery led the lithium secondary battery to have a high capacity.

Example 16

Pentaglyme

As in Example 1, 4.8699 g of sulfur (Kanto Chemical Co., Inc.; 99%) and 2.0591 g of polyethylene glycol dimethyl ether (pentaglyme, Aldrich, average molecular weight: 250) were placed in a test tube (inner diameter: 30 mm; length:

300 mm), and heating was performed in an electric furnace under nitrogen stream for 1 hour until the sample temperature reached 435° C. The obtained reaction product was put in a quartz boat, which was disposed inside a quartz tube to vaporize and remove sulfur under a flow of nitrogen at 300° C. for 2 hours. In this manner, 0.3146 g of black solid powder was obtained.

The thus obtained organic sulfur material was analyzed by Raman spectroscopy, XAFS spectroscopy, and TG-DTA, as in Example 1. The results were the same as those obtained in Example 1. Specifically, an organic sulfur material containing a component that has undergone carbonization and having excellent heat resistance was obtained, the material having carbon and sulfur interactions.

Figure 21:
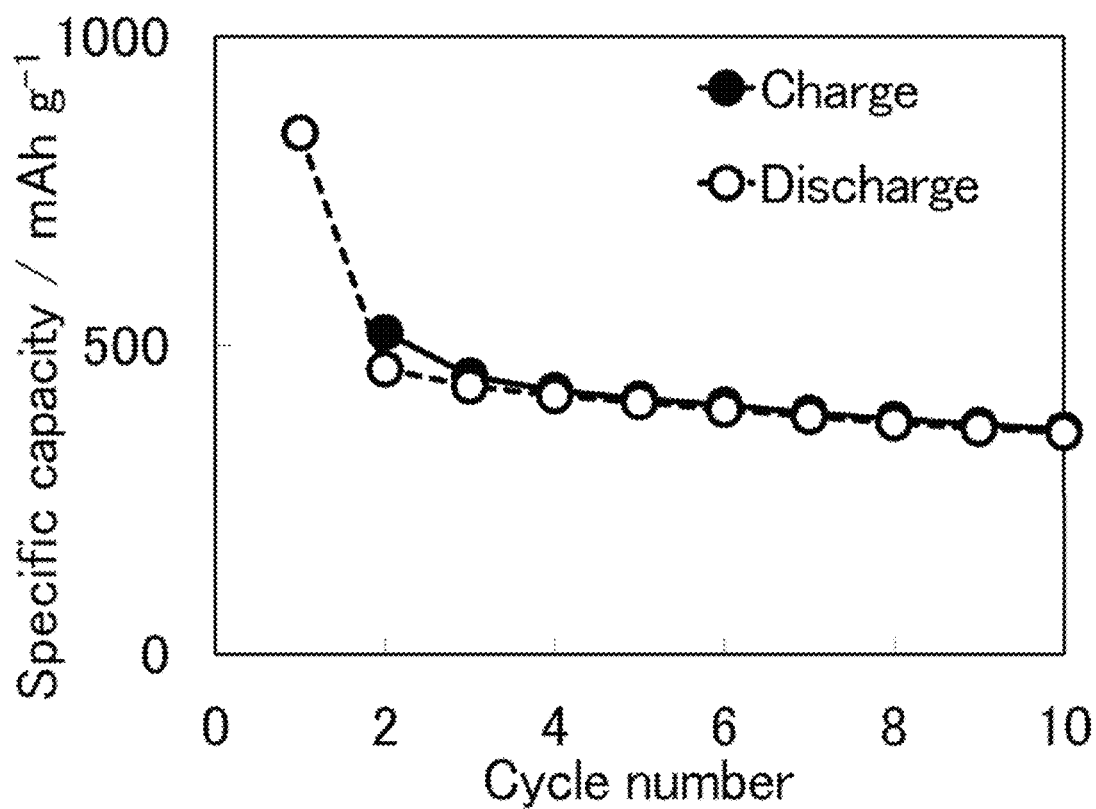
FIG. 21 is a graph showing the charge and discharge test results of the non-aqueous electrolyte lithium secondary battery obtained in Example 16.

The charge and discharge test was conducted in completely the same manner as in Example 1, except that this organic sulfur material was used as a cathode active material of a non-aqueous electrolyte lithium secondary battery. FIG. 21 shows the charge and discharge characteristics. The initial discharge capacity was about 840 mAh/g, which was higher than that of the organic sulfur material obtained using polyacrylonitrile (PAN) as a starting material (Comparative Example 1; about 720 mAh/g). Further, the initial charge capacity was about 520 mAh/g, which was higher than that of the organic sulfur material obtained using polyacrylonitrile (PAN) as a starting material (Comparative Example 1; about 430 mAh/g).

The results indicate that the production of an organic sulfur material under the conditions adopted in the present invention and use of the organic sulfur material as a cathode active material of a non-aqueous electrolyte lithium secondary battery led the lithium secondary battery to have a high capacity.

Example 17

Octaglyme

As in Example 1, 4.8852 g of sulfur (Kishida Chemical Co., Ltd.; 99%) and 1.6494 g of polyethylene glycol dimethyl ether (octaglyme, Aldrich, average molecular weight: 500) were placed in a test tube (inner diameter: 30 mm; length: 300 mm), and heating was performed in an electric furnace under nitrogen stream for 1 hour until the sample temperature reached 438° C. The obtained reaction product was put in a quartz boat, which was disposed inside a quartz tube to vaporize and remove sulfur under a flow of nitrogen at 300° C. for 1.5 hours. In this manner, 0.3773 g of black solid powder was obtained.

The thus obtained organic sulfur material was analyzed by Raman spectroscopy, XAFS spectroscopy, and TG-DTA, as in Example 1. The results were the same as those obtained in Example 1. Specifically, an organic sulfur material containing a component that has undergone carbonization and having excellent heat resistance was obtained, the material having carbon and sulfur interactions.

Figure 22:
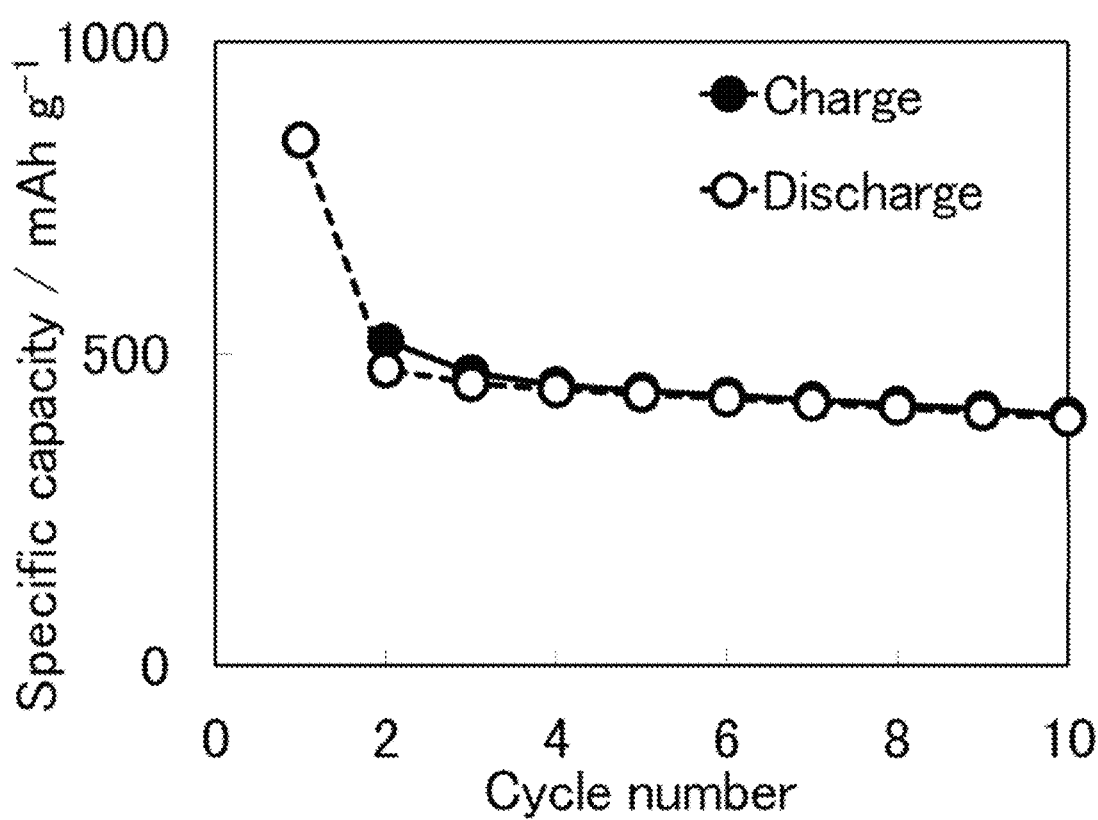
FIG. 22 is a graph showing the charge and discharge test results of the non-aqueous electrolyte lithium secondary battery obtained in Example 17.

The charge and discharge test was conducted in completely the same manner as in Example 1, except that this organic sulfur material was used as a cathode active material of a non-aqueous electrolyte lithium secondary battery. FIG. 22 shows the charge and discharge characteristics. The initial discharge capacity was about 840 mAh/g, which was higher than that of the organic sulfur material obtained using polyacrylonitrile (PAN) as a starting material (Comparative Example 1; about 720 mAh/g). Further, the initial charge capacity was about 520 mAh/g, which was higher than that of the organic sulfur material obtained using polyacrylonitrile (PAN) as a starting material (Comparative Example 1; about 430 mAh/g).

The results indicate that the production of an organic sulfur material under the conditions adopted in the present invention and use of the organic sulfur material as a cathode active material of a non-aqueous electrolyte lithium secondary battery led the lithium secondary battery to have a high capacity.

Example 18

Icosaglyme

As in Example 1, 47.2 g of sulfur (Kanto Chemical Co., Inc.; 99%) and 26.0 g of polyethylene glycol dimethyl ether (icosaglyme, Aldrich, average molecular weight: 1000) were placed in an alumina Tammann tube (inner diameter: 50 mm; length: 180 mm), and heating was performed in an electric furnace under nitrogen stream for 1 hour until the sample temperature reached 308° C. The obtained reaction product was put in a quartz boat, which was disposed inside a quartz tube to vaporize and remove sulfur under a flow of nitrogen at 300° C. for 5 hours. In this manner, 9.7693 g of black solid powder was obtained.

The thus obtained organic sulfur material was analyzed by Raman spectroscopy, XAFS spectroscopy, and TG-DTA, as in Example 1. The results were the same as those obtained in Example 1. Specifically, an organic sulfur material containing a component that has undergone carbonization and having excellent heat resistance was obtained, the material having carbon and sulfur interactions.

Figure 23:
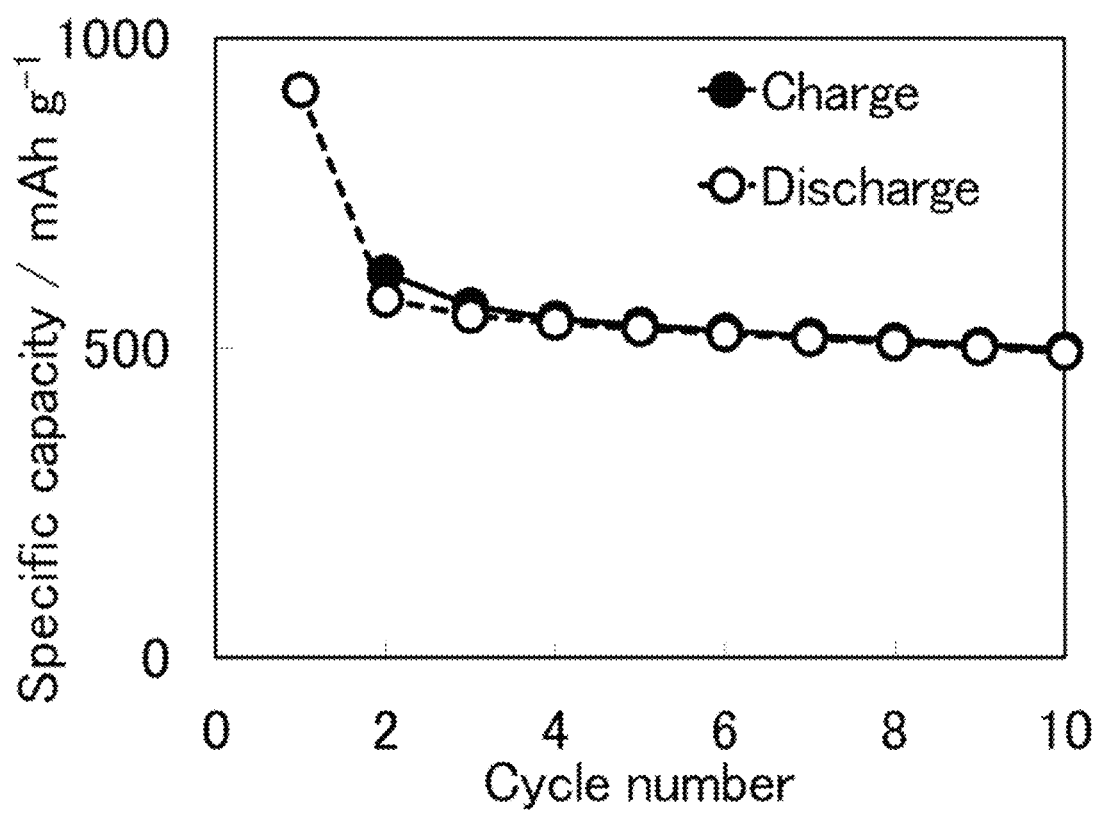
FIG. 23 is a graph showing the charge and discharge test results of the non-aqueous electrolyte lithium secondary battery obtained in Example 18.

The charge and discharge test was conducted in completely the same manner as in Example 1, except that this organic sulfur material was used as a cathode active material of a non-aqueous electrolyte lithium secondary battery. FIG. 23 shows the charge and discharge characteristics. The initial discharge capacity was about 910 mAh/g, which was higher than that of the organic sulfur material obtained using polyacrylonitrile (PAN) as a starting material (Comparative Example 1; about 720 mAh/g). Further, the initial charge capacity was about 620 mAh/g, which was higher than that of the organic sulfur material obtained using polyacrylonitrile (PAN) as a starting material (Comparative Example 1; about 430 mAh/g).

The results indicate that the production of an organic sulfur material under the conditions adopted in the present invention and use of the organic sulfur material as a cathode active material of a non-aqueous electrolyte lithium secondary battery led the lithium secondary battery to have a high capacity.

Example 19

Polyethylene Glycol 200 ($LiPF_6$ Electrolyte Solution)

A battery was produced in completely the same manner as in Example 1, except for the electrolyte solution and the use of the organic sulfur material obtained in Example 2 as a cathode active material. Subsequently, a charge and discharge test was conducted. The electrolyte solution was prepared as follows: lithium hexafluorophosphate was dissolved in a mixed solvent of ethylene carbonate and diethyl carbonate with volume ratio of 1:1 to a concentration of 1 M.

Figure 24:
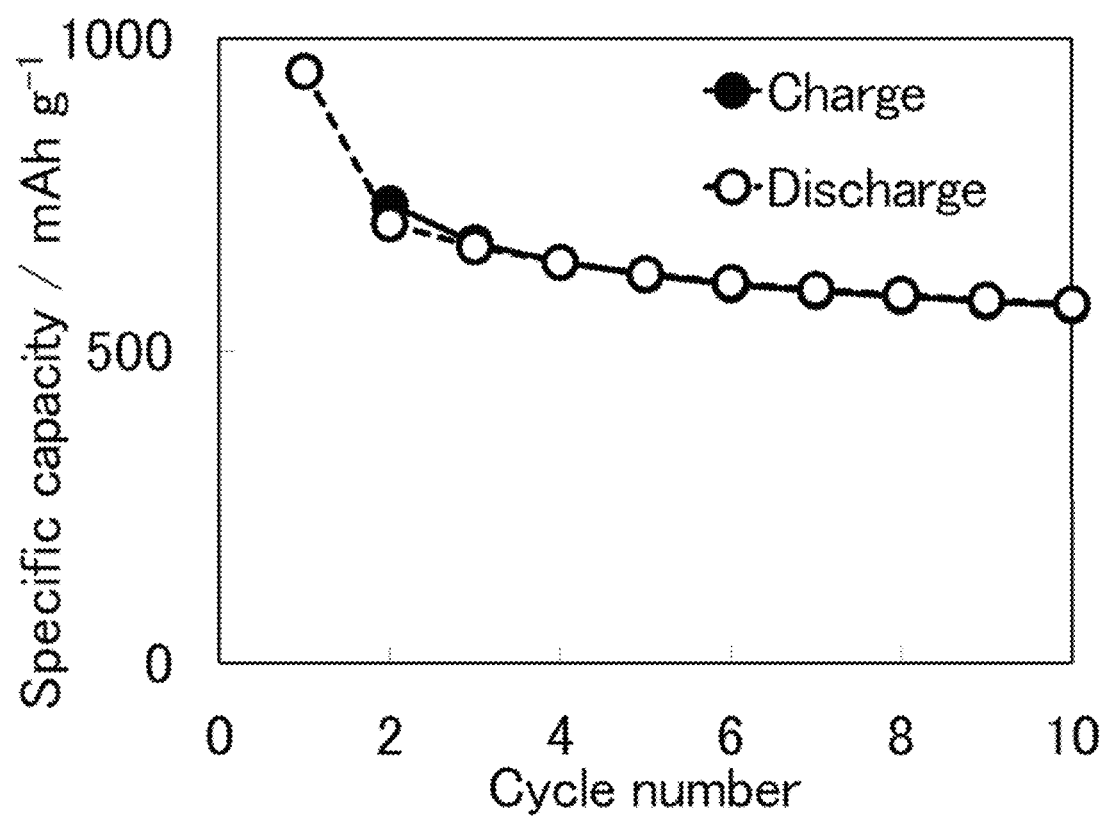
FIG. 24 is a graph showing the charge and discharge test results of the non-aqueous electrolyte lithium secondary battery obtained in Example 19.

FIG. 24 shows the charge and discharge characteristics. The initial discharge capacity was about 940 mAh/g, while the initial charge capacity was about 730 mAh/g, showing a high capacity.

The results indicate that when $LiPF_6$ was used as an electrolyte, the production of an organic sulfur material under the conditions adopted in the present invention and use of the organic sulfur material as a cathode active material of a non-aqueous electrolyte lithium secondary battery also led the lithium secondary battery to have a high capacity.

Example 20

Polyethylene Glycol 6000 ($LiPF_6$ Electrolyte Solution)

A battery was produced in completely the same manner as in Example 1, except for the electrolyte solution and the use of the organic sulfur material obtained in Example 14 as a cathode active material. Subsequently, a charge and discharge test was conducted.

The electrolyte solution was prepared as follows: lithium hexafluorophosphate was dissolved in a mixed solvent of ethylene carbonate and diethyl carbonate with volume ratio of 1:1 to a concentration of 1 M.

Figure 25:
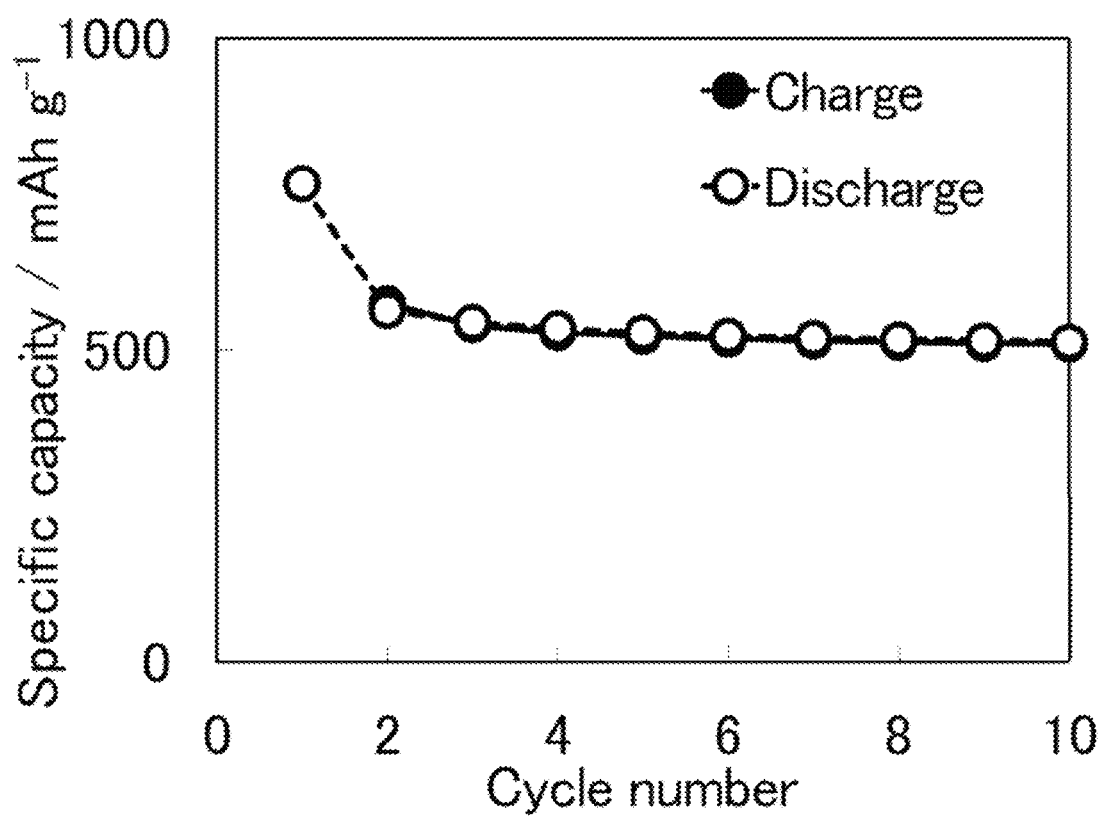
FIG. 25 is a graph showing the charge and discharge test results of the non-aqueous electrolyte lithium secondary battery obtained in Example 20.

FIG. 25 shows the charge and discharge characteristics. The initial discharge capacity was about 760 mAh/g, while the initial charge capacity was about 570 mAh/g, showing a high capacity.

The results indicate that when $LiPF_6$ was used as an electrolyte, the production of an organic sulfur material under the conditions adopted in the present invention and use of the organic sulfur material as a cathode active material of a non-aqueous electrolyte lithium secondary battery also led the lithium secondary battery to have a high capacity.

Example 21

Large-Volume Synthesis of Polyethylene Glycol 200 ($LiPF_6$ Electrolyte Solution, $LiCoO_2$ Cathode)

The organic sulfur material obtained in Example 2 was used as an anode and mixed in an agate mortar, such that the organic sulfur material:acetylene black:polytetrafluoroethylene (PTFE)=5:4:1 (weight ratio). The resulting mixture was compression-bonded to an aluminum mesh as a collector to thus obtain an anode. A cathode was obtained by mixing of lithium cobalt oxide ($LiCoO_2$), acetylene black, and PTFE at a weight ratio of 84:8:8 in an agate mortar, and compression bonding of the resulting mixture to an aluminum mesh as a collector. Further, an electrolyte solution obtained by dissolving lithium hexafluorophosphate in a mixed solvent (ethylene carbonate/diethyl carbonate, volume ratio: 1:1) to a concentration of 1 M was used. The charge and discharge test was conducted at a cutoff voltage of 1.0 to 3.0 V by starting from charge and in completely the same manner as in Example 1, except for the conditions stated here.

Figure 26:
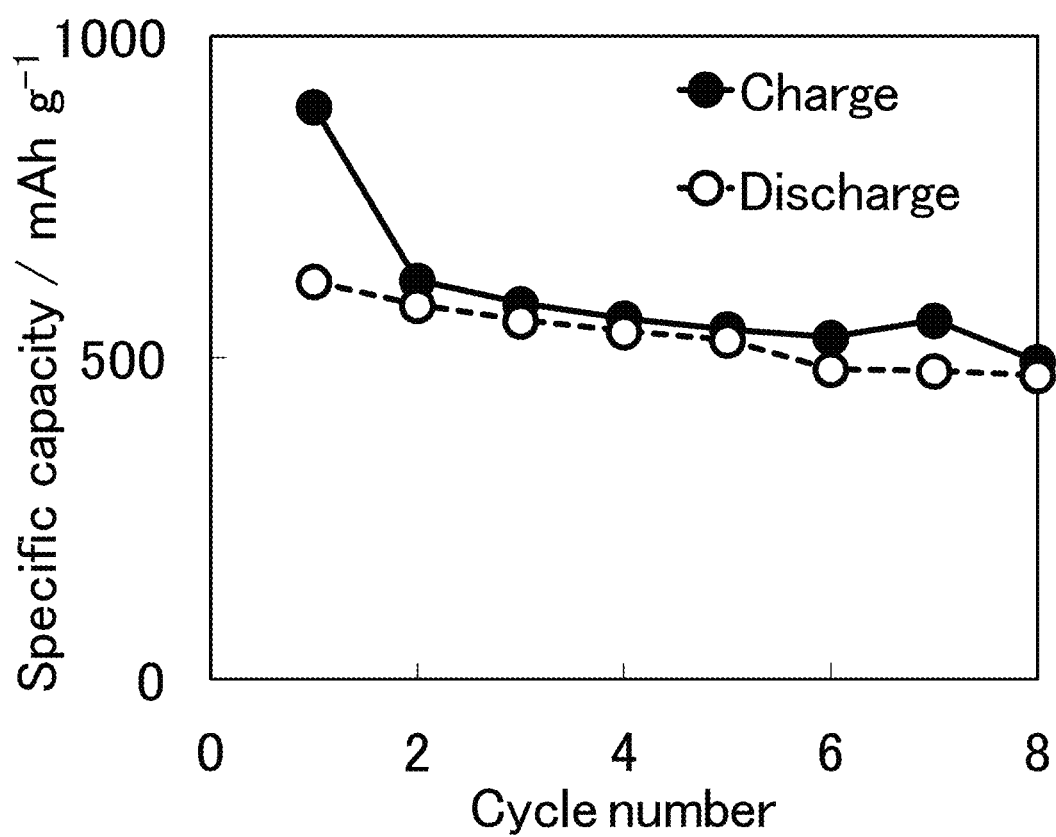
FIG. 26 is a graph showing the charge and discharge test results of the non-aqueous electrolyte lithium-ion secondary battery obtained in Example 21.

FIG. 26 shows the charge and discharge characteristics. The initial charge capacity was about 890 mAh/g, while the initial discharge capacity was about 610 mAh/g, showing a high capacity.

The results indicate that when $LiPF_6$ was used as an electrolyte and $LiCoO_2$ as a cathode, the production of an organic sulfur material under the conditions adopted in the present invention and use of the organic sulfur material as an anode material of a non-aqueous electrolyte lithium-ion secondary battery led the lithium-ion secondary battery to have a high capacity.

Example 22

Large-Volume Synthesis of Polyethylene Glycol 200 ($NaPF_6$ Electrolyte Solution, Na Anode)

Figure 27:
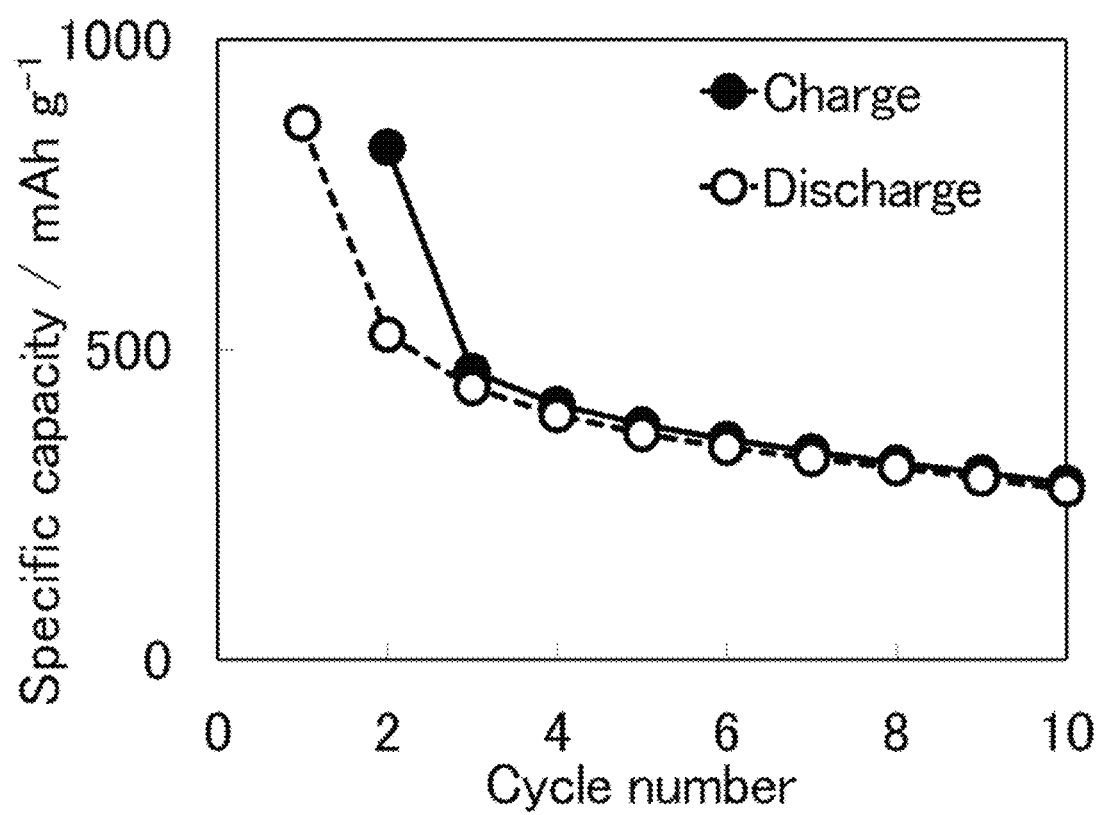
FIG. 27 is a graph showing the charge and discharge test results of the non-aqueous electrolyte sodium secondary battery obtained in Example 22.

The charge and discharge test was conducted in completely the same manner as in Example 1, except that the organic sulfur material obtained in Example 2 was used, a metal sodium was used as an anode, an electrolyte solution obtained by dissolving sodium hexafluorophosphate in a mixed solvent (ethylene carbonate/diethyl carbonate, volume ratio 1:1) to a concentration of 1 M was used, and the cutoff voltage was adjusted to 0.7 to 2.7 V. FIG. 27 shows the charge and discharge characteristics. The initial discharge capacity was about 860 mAh/g, while the initial charge capacity was about 820 mAh/g, showing a high capacity.

The results indicate that when $NaPF_6$ was used as an electrolyte and Na as an anode, the production of an organic sulfur material under the conditions adopted in the present invention and use of the organic sulfur material as a cathode active material of a non-aqueous electrolyte sodium secondary battery led the sodium secondary battery to have a high capacity.

Example 23

Large-Volume Synthesis of Polyethylene Glycol 200 ($NaPF_6$ Electrolyte Solution, $NaFeO_2$ Cathode)

The organic sulfur material obtained in the Example 2 was used as an anode and mixed in an agate mortar, such that the organic sulfur material:acetylene black:polytetrafluoroethylene (PTFE)=5:4:1 (weight ratio). The resulting mixture was compression-bonded to an aluminum mesh as a collector to thus obtain an anode. A cathode was obtained by mixing of sodium ferrate ($NaFeO_2$), acetylene black, and PTFE at a weight ratio of 84:8:8 in an agate mortar, and compression bonding of the resulting mixture to an aluminum mesh as a collector. Further, an electrolyte solution obtained by dissolving sodium hexafluorophosphate in a mixed solvent (ethylene carbonate/diethyl carbonate, volume ratio: 1:1) to a concentration of 1 M was used. The charge and discharge test was conducted at a cutoff voltage of 1.0 to 3.0 V by starting from charge and in completely the same manner as in Example 1, except for the conditions stated here.

Figure 28:
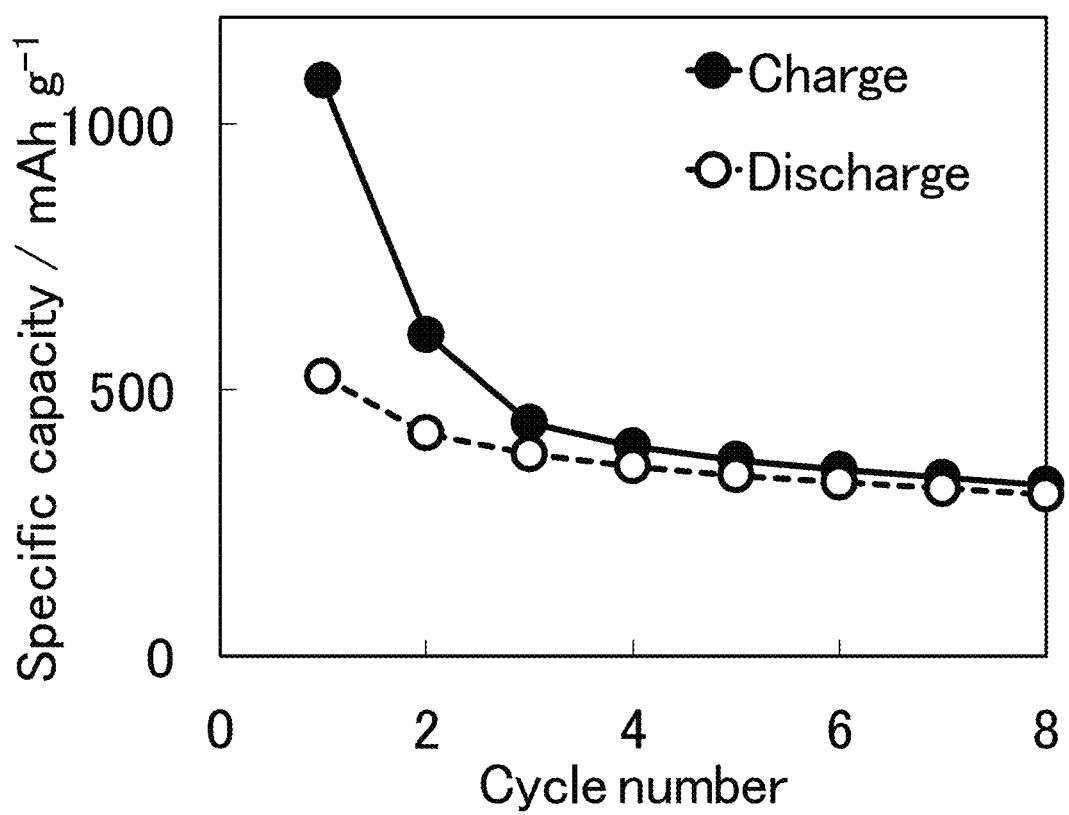
FIG. 28 is a graph showing the charge and discharge test results of the non-aqueous electrolyte sodium-ion secondary battery obtained in Example 23.

FIG. 28 shows the charge and discharge characteristics. The initial charge capacity was about 1080 mAh/g, and the initial discharge capacity was about 520 mAh/g, showing a high capacity.

The results indicate that the production of an organic sulfur material under the conditions adopted in the present invention and use of the organic sulfur material as an anode material of a non-aqueous electrolyte sodium-ion secondary battery led the sodium-ion secondary battery to have a high capacity.

Example 24

Large-Volume Synthesis of Polyethylene Glycol 200 ($Mg(TFSA)_2$ electrolyte solution, Mg anode)

Figure 29:
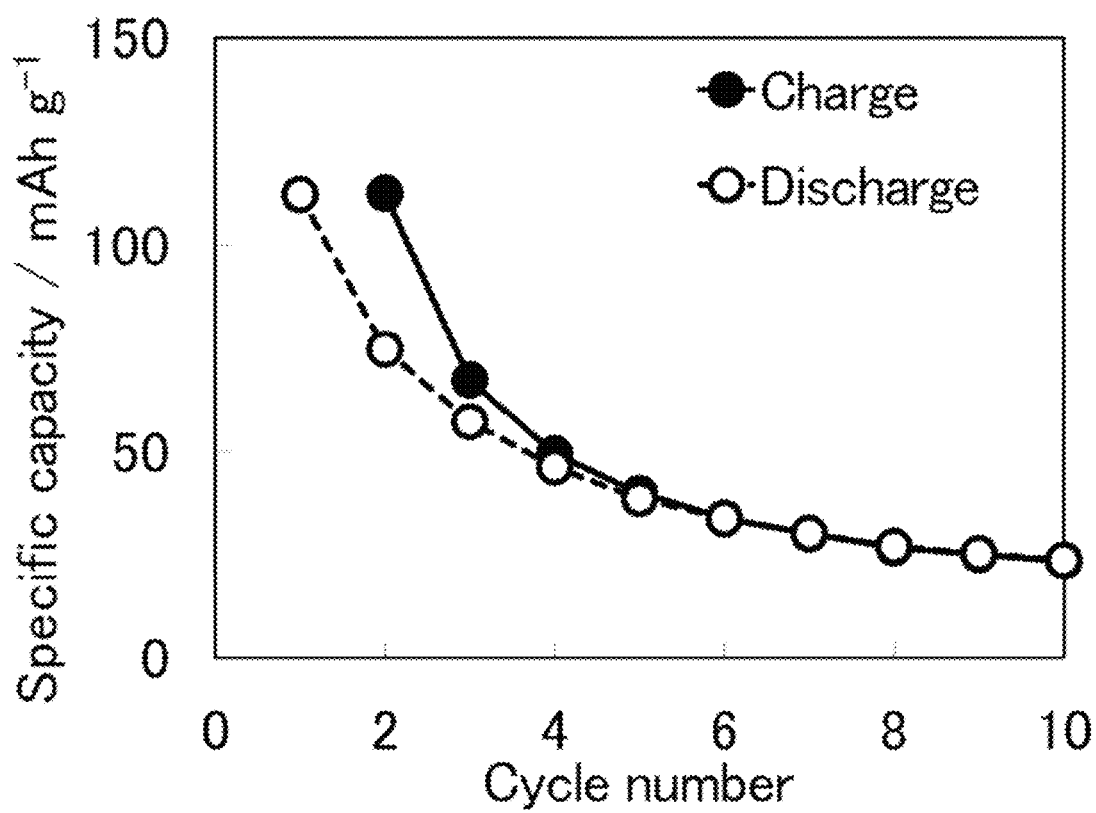
FIG. 29 is a graph showing the charge and discharge test results of the non-aqueous electrolyte magnesium secondary battery obtained in Example 24.

The charge and discharge test was conducted in completely the same manner as in Example 1, except that the organic sulfur material obtained in the Example 2 was used, a metal magnesium was used as an anode, an electrolyte solution obtained by dissolving magnesium trifluoromethanesulfonyl amide (Mg(TFSA)$_2$) in ethylene glycol dimethyl ether to a concentration of 0.4 M was used, and the cutoff voltage was adjusted to −1.0 to 2.3 V. FIG. 29 shows the charge and discharge characteristics. The initial discharge capacity was about 110 mAh/g, while the initial charge capacity was about 110 mAh/g. When Mg$_x$Mo$_3$S$_4$ is used as a cathode active material of a full-cell magnesium secondary battery disclosed in the document that is cited the most for a full-cell magnesium secondary battery (D. Aurbach et al., Nature, 407, 724, (2000)), the capacity is a little less than 100 mAh/g. Compared with this capacity, the capacity achieved in Example 24 was excellent; thus, the organic sulfur material of the present invention is also useful as a cathode active material for a magnesium secondary battery.

The invention claimed is:

1. An organic sulfur material comprising carbon, hydrogen, oxygen, and sulfur as constituent elements, and having peaks of 482±50 cm$^{-1}$, 846±50 cm$^{-1}$, 1066±50 cm$^{-1}$, 1279±50 cm$^{-1}$, and 1442±50 cm$^{-1}$ in a Raman spectrum detected by Raman spectroscopy, the peak of 1442±50 cm$^{-1}$ being of highest intensity in the Raman spectrum, wherein the organic sulfur material has a carbon content of 20 to 50 wt %, a hydrogen content of 0.01 to 5 wt %, an oxygen content of 0.1 to 30 wt %, and a sulfur content of 45 to 75 wt %.

2. The organic sulfur material according to claim 1, wherein the intensities of the Raman scattering peaks of 482±50 cm$^{-1}$, 846±50 cm$^{-1}$, 1066±50 cm$^{-1}$, and 1279±50 cm$^{-1}$ are each 0.4 times, or less, the intensity of the Raman scattering peak of 1442±50 cm$^{-1}$.

3. The organic sulfur material according to claim 1, further having peaks of Raman scattering intensity in the vicinity of 770±50 cm$^{-1}$ and/or 1924±50 cm$^{-1}$ in the Raman spectrum detected by Raman spectroscopy.

4. The organic sulfur material according to claim 1, having peaks in the vicinity of 2469.2 eV, 2472.0 eV, and 2473.2 eV in an X-ray absorption fine structure spectrum, the peak intensity in the vicinity of 2472.0 eV and the peak intensity in the vicinity of 2473.2 eV being both 2 times, or more, the peak intensity in the vicinity of 2469.2 eV.

5. An electrode active material for a battery, the material comprising the organic sulfur material of claim 1.

6. The electrode active material for a battery according to claim 5, which is an electrode active material for a lithium-ion secondary battery or a sodium-ion secondary battery.

7. A battery comprising, as a constituent element, the electrode active material for a battery of claim 5.

8. The battery according to claim 7, which is a lithium-ion secondary battery or a sodium-ion secondary battery.

9. An all-solid-state lithium-ion secondary battery or an all-solid-state sodium-ion secondary battery, comprising as constituent elements, the electrode active material for a battery of claim 5, and a lithium-ion conductive solid electrolyte or a sodium-ion conductive solid electrolyte.

10. The all-solid-state lithium-ion secondary battery or the all-solid-state sodium-ion secondary battery according to claim 9, wherein the lithium-ion conductive solid electrolyte or the sodium-ion conductive solid electrolyte contains an inorganic compound containing sulfur as a constituent element.

11. A method for producing an organic sulfur material comprising carbon, hydrogen, oxygen, and sulfur as constituent elements, and having peaks of 482±50 cm$^{-1}$, 846±50 cm$^{-1}$, 1066±50 cm$^{-1}$, 1279±50 cm$^{-1}$, and 1442±50 cm$^{-1}$ in a Raman spectrum detected by Raman spectroscopy, the peak of 1442±50 cm$^{-1}$ being of highest intensity in the Raman spectrum and the organic sulfur material having a carbon content of 20 to 50 wt %, a hydrogen content of 0.01 to 5 wt %, an oxygen content of 0.1 to 30 wt %, and a sulfur content of 45 to 75 wt %, the method comprising the step of subjecting a solution containing a sulfur-containing starting material and polyethylene glycol or a derivative thereof to heat treatment in an inert atmosphere.

12. The production method according to claim 11, wherein the heat treatment step comprises refluxing at 250° C. or higher the solution containing a sulfur-containing starting material and polyethylene glycol or a derivative thereof.

13. The production method according to claim 11, wherein the method comprises the step of performing heating at 200 to 450° C. under an inert gas stream after the heat treatment step.

* * * * *